United States Patent
Boggs et al.

(10) Patent No.: US 7,419,997 B2
(45) Date of Patent: Sep. 2, 2008

(54) TETRAHYDROCARBAZOLE DERIVATIVES AND THEIR PHARMACEUTICAL USE

(75) Inventors: Sharon Davis Boggs, Durham, NC (US); Kristjan S Gudmundsson, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/560,016

(22) PCT Filed: Jun. 7, 2004

(86) PCT No.: PCT/US2004/018180

§ 371 (c)(1),
(2), (4) Date: Dec. 8, 2005

(87) PCT Pub. No.: WO2005/005386

PCT Pub. Date: Jan. 20, 2005

(65) Prior Publication Data

US 2006/0148857 A1  Jul. 6, 2006

Related U.S. Application Data

(60) Provisional application No. 60/497,787, filed on Aug. 26, 2003, provisional application No. 60/477,972, filed on Jun. 12, 2003.

(51) Int. Cl.
| | | |
|---|---|---|
| *A61K 31/403* | (2006.01) | |
| *A61K 31/4155* | (2006.01) | |
| *A61K 31/4178* | (2006.01) | |
| *A61K 31/4439* | (2006.01) | |
| *C07D 209/82* | (2006.01) | |
| *C07D 403/12* | (2006.01) | |
| *C07D 233/90* | (2006.01) | |
| *C07D 213/74* | (2006.01) | |

(52) U.S. Cl. .............. 514/411; 514/406; 514/397; 514/339; 548/439; 548/311.4; 548/364.7

(58) Field of Classification Search .......... 548/311.4, 548/364.7, 439; 546/276.7; 514/411, 406, 514/397, 339
See application file for complete search history.

(56) References Cited

U.S. PATENT DOCUMENTS

2003/0232873 A1  12/2003 Koppitz et al.

FOREIGN PATENT DOCUMENTS

| EP | 0 451 634 | 10/1991 |
| EP | 0 496 314 | 7/1992 |
| WO | 02/00632 | 1/2002 |

OTHER PUBLICATIONS

Bernard, H. (J. of Antimicrobial Chemotherapy 2004, 53, 137-139).*
Eash et al. (Cell. Mol. Life. Sci. 2006, 63, 865-876).*
A. Bailey, "Further examination of the reactions between arenesulphonyl azides and tetrahydrocarbazoles," *Journal of the Chemical Society, Perkin Trans I*, V17, 1973, pp. 1809-1818.
Database Chemcats Chemical Abstract Service, Columbus, OH, XP002300241 order Nos. 5781459 and 5781444.
"Chembridge screening library", May 19, 2004, Chembridge Corporation, 16981 Via Tazon, Suite G, San Diego, CA 92127.

* cited by examiner

*Primary Examiner*—Rebecca L Anderson
*Assistant Examiner*—Jason M Nolan
(74) *Attorney, Agent, or Firm*—Karen L. Prus

(57) ABSTRACT

The present invention relates to novel compounds that are useful in the treatment of human papillomaviruses, and also to the methods for the making and use of such compounds.

27 Claims, No Drawings

TETRAHYDROCARBAZOLE DERIVATIVES AND THEIR PHARMACEUTICAL USE

This application is filed pursuant to 35 U.S.C. § 371 as a United States National Phase Application of International Application No. PCT/US2004/018180 filed Jun. 7, 2004, which claims priority from U.S. 60/477,972 filed Jun. 12, 2003 and U.S. 60/497,787 filed Aug. 26, 2003.

FIELD OF THE INVENTION

The present invention relates to novel compounds that are useful in the treatment of human papillomaviruses, and also to the methods for the making and use of such compounds.

BACKGROUND OF THE INVENTION

Human Papillomaviruses (HPVs) are small nonenveloped DNA viruses involved in many conditions and diseases. For example HPVs cause a wide variety of benign and pre-malignant tumors.

HPV is spread by direct contact. HPVs may be divided into two categories: cutaneous and mucosal. The cutaneous HPVs cause warts on hands and feet, such as common, plantar, filiform, or flat warts. The mucosal HPV types infect the anogenital region and the oral cavity. Approximately 100 different types of HPV have been characterized to date. Approximately 40 HPV types specifically infect the genital and oral mucosa.

Mucosal HPVs are most frequently sexually transmitted and, with an incidence roughly twice that of herpes simplex virus infection, HPVs are considered one of the most common sexually transmitted diseases (STDs) throughout the world. Infection with the human papillomavirus (HPV) may not cause any symptoms and does not always produce visible genital warts. When symptoms do develop, they usually occur 2 to 3 months after infection with the virus. Symptoms have been known to develop, however, from 3 weeks to many years after infection occurs. As such, HPV may be spread unknowingly.

More than 25 HPV types that are implicated in anogenital diseases are broadly classified as either low risk or high risk. Low risk HPVs, such as HPV-6 and HPV-11, are the etiological cause of genital warts (condyloma acuminata). High risk HPVs, such as HPV-16, 18, 31, 33, 35, 39, 45, 51, 52, 56, 58, 59, and 68, usually do not produce visible genital warts. Rather the high-risk viral types may be identified by DNA testing. High risk HPVs such as HPV-16 and HPV-18 may be found on Pap screening tests and be related to precancerous cervical cell change, cervical dysplasia, and cervical cancer. In fact, high-risk HPV types, such as 16, 18, 31, 33, and 35, are strongly associated with precancerous and cancerous changes of the cervix. Most cervical cancers (about 90%) contain one of these high-risk types. High risk HPV infection creates a lifetime risk of invasive cancer in the range of 5-10% for untreated infection.

In addition to cervical cancer, high risk HPVs are associated with a number of anal and perianal cancers.

Current treatments for genital warts and cervical dysplasia include physical removal such as cryotherapy, electrosurgery, and surgical excision. Currently, there are no effective antiviral treatments for HPV infection.

SUMMARY OF THE INVENTION

The present invention includes compounds of formula (I):

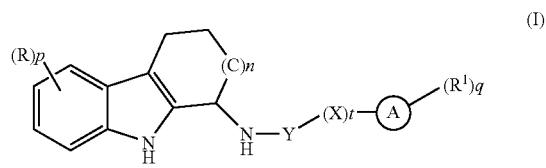

wherein
n is 0, 1, or 2;
t is 0 or 1;
X is —NH—, —O—, —R$^{10}$—, —OR$^{10}$—, —R$^{10}$O—, —R$^{10}$OR$^{10}$—, —NR$^{10}$—, —R$^{10}$N—, —R$^{10}$NR$^{10}$—, R$^{10}$S(O)$_m$—, or —R$^{10}$S(O)$_m$R$^{10}$—;
Y is —C(O)— or —S(O)$_m$—;
each R is the same or different and is independently selected from the group consisting of halogen, haloalkyl, alkyl, alkenyl, alkynyl, cycloalkyl, cycloalkenyl, —R$^{10}$cycloalkyl, Ay, —NHR$^{10}$Ay, Het, —NHHet, —NHR$^{10}$Het, —OR$^2$, —OAy, —OHet, —R$^{10}$OR$^2$, —NR$^2$R$^3$, —NR$^2$Ay, —R$^{10}$NR$^2$R$^3$, —R$^{10}$NR$^2$Ay, —R$^{10}$C(O)R$^2$, —C(O)R$^2$, —CO$_2$R$^2$, —R$^{10}$CO$_2$R$^2$, —C(O)NR$^2$R$^3$, —C(O)Ay, —C(O)NR$^2$Ay, —C(O)Het, —C(O)NHR$^{10}$Het, —R$^{10}$C(O)NR$^2$R$^3$, —C(S)NR$^2$R$^3$, —R$^{10}$C(S)NR$^2$R$^3$, —R$^{10}$NHC(NH)NR$^2$R$^3$, —C(NH)NR$^2$R$^3$, —R$^{10}$C(NH)NR$^2$R$^3$, —S(O)$_2$NR$^2$R$^3$, —S(O)$_2$NR$^2$Ay, —R$^{10}$SO$_2$NHCOR$^2$, —R$^{10}$SO$_2$NR$^2$R$^3$, —R$^{10}$SO$_2$R$^2$, —S(O)$_m$R$^2$, —S(O)$_m$Ay, cyano, nitro, or azido;
each R$^1$ is the same or different and is independently selected from the group consisting of halogen, haloalkyl, alkyl, alkenyl, alkynyl, cycloalkyl, cycloalkenyl, —R$^{10}$cycloalkyl, Ay, —NHR$^{10}$Ay, Het, —NHHet, —NHR$^{10}$Het, —OR$^2$, —OAy, —OHet, —R$^{10}$OR$^2$, —NR$^2$R$^3$, —NR$^2$Ay, —R$^{10}$NR$^2$R$^3$, —R$^{10}$NR$^2$Ay, —R$^{10}$C(O)R$^2$, —C(O)R$^2$, —CO$_2$R$^2$, —R$^{10}$CO$_2$R$^2$, —C(O)NR$^2$R$^3$, —C(O)Ay, —C(O)NR$^2$Ay, —C(O)Het, —C(O)NHR$^{10}$Het, —R$^{10}$C(O)NR$^2$R$^3$, —C(S)NR$^2$R$^3$, —R$^{10}$C(S)NR$^2$R$^3$, —R$^{10}$NHC(NH)NR$^2$R$^3$, —C(NH)NR$^2$R$^3$, —R$^{10}$C(NH)NR$^2$R$^3$, —S(O)$_2$NR$^2$R$^3$, —S(O)$_2$NR$^2$Ay, —R$^{10}$SO$_2$NHCOR$^2$, —R$^{10}$SO$_2$NR$^2$R$^3$, —R$^{10}$SO$_2$R$^2$, —S(O)$_m$R$^2$, —S(O)$_m$Ay, cyano, nitro, or azido;
each m independently is 0, 1, or 2;
each R$^{10}$ is the same or different and is independently selected from alkylene, cycloalkylene, alkenylene, cycloalkenylene, and alkynylene;
p and q are each independently selected from 0, 1, 2, 3, 4, or 5;
each of R$^2$ and R$^3$ are the same or different and are independently selected from the group consisting of H, alkyl, alkenyl, alkynyl, cycloalkyl, cycloalkenyl, —R$^{10}$cycloalkyl, —R$^{10}$OH, —R$^{10}$(OR$^{10}$)$_w$, and —R$^{10}$NR$^4$R$^5$;
w is 1-10;
each of R$^4$ and R$^5$ are the same or different and are independently selected from the group consisting of alkyl, cycloalkyl, alkenyl, cycloalkenyl, and alkynyl;
Ay represents an aryl group;
Het represents a 5- or 6-membered heterocyclyl or heteroaryl group;
ring A is aryl or heteroaryl;
provided that when the A ring is aryl, t is 0, and Y is SO$_2$, then p is not 0; and salts, solvates and physiologically functional derivatives thereof.

Preferably, in describing the present invention in more detail, alkyl is $C_1$-$C_6$ alkyl, alkoxy is $C_1$-$C_6$ alkoxy, haloalkyl is $C_1$-$C_6$ haloalkyl, alkylene is $C_1$-$C_6$ alkylene, and alkenylene is $C_1$-$C_6$ alkenylene.

In one embodiment t is 0 and Y is —C(O)—. In another embodiment t is 0 and Y is —S(O)$_m$—.

In one embodiment t is 1, Y is —C(O)—, and X is —NH—, —O—, —$R^{10}$—, or —O$R^{10}$—. In another embodiment t is 1, Y is —S(O)$_m$—, and X is —NH—, —O—, —$R^{10}$—, or —O$R^{10}$—.

In one embodiment preferably n is 1.

Preferably p is 1 or more and when p is 1 or more, R is selected from halogen, alkyl, haloalkyl, —O$R^2$, —N$R^2R^3$, —C(O)$R^2$, —CO$_2R^2$, cyano, nitro, or azido. More preferably R is halogen, alkyl, haloalkyl. More preferably R is substituted para to the depicted N atom. More preferably R is halogen. More preferably R is Br or Cl.

Preferably q is one or more and when q is 1 or more, $R^1$ is selected from halogen, alkyl, haloalkyl, —O$R^2$, —N$R^2R^3$, —C(O)$R^2$, —CO$_2R^2$, Ay, Het, cyano, nitro, or azido. More preferably $R^1$ is selected from halogen, alkyl, haloalkyl, —O$R^2$, —N$R^2R^3$, —C(O)$R^2$, —CO$_2R^2$, or cyano. Preferably $R^2$ and $R^3$ each are $C_1$-$C_6$ alkyl. More preferably $R^1$ is selected from halogen, alkyl, or —O$R^2$. More preferably said halogen is fluoro or chloro, said alkyl is methyl, and said —O$R^2$ is alkoxy.

In one embodiment preferably the A ring is aryl. Preferably the A ring is phenyl. Further preferably q is 1 or more and $R^1$ is selected from halogen, alkyl, haloalkyl, —O$R^2$, —N$R^2R^3$, —C(O)$R^2$, —CO$_2R^2$, Ay, Het, cyano, nitro, or azido. More preferably $R^1$ is selected from halogen, alkyl, haloalkyl, —O$R^2$, —N$R^2R^3$, —C(O)$R^2$, —CO$_2R^2$, or cyano.

In another embodiment the A ring is heteroaryl. Preferably the heteroaryl is pyridyl. Preferably q is 0 or 1. Preferably when q is 1, then $R^1$ is is selected from halogen, alkyl, haloalkyl, —O$R^2$, —N$R^2R^3$, —C(O)$R^2$, —CO$_2R^2$, Ay, Het, cyano, nitro, or azido. More preferably when q is 1, then $R^1$ is is selected from halogen, alkyl, haloalkyl, —O$R^2$, —N$R^2R^3$, —C(O)$R^2$, —CO$_2R^2$, or cyano.

In another embodiment, p is 1, R is halogen, n is 1, Y is —C(O)—, t is 0, ring A is heteroaryl, and q is 0. Preferably R is chloro or bromo and ring A is pyridyl.

One embodiment includes a compound selected from:

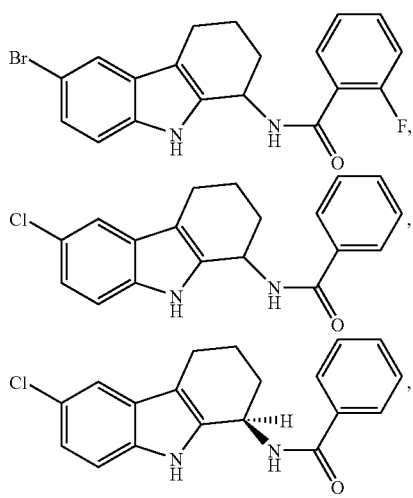

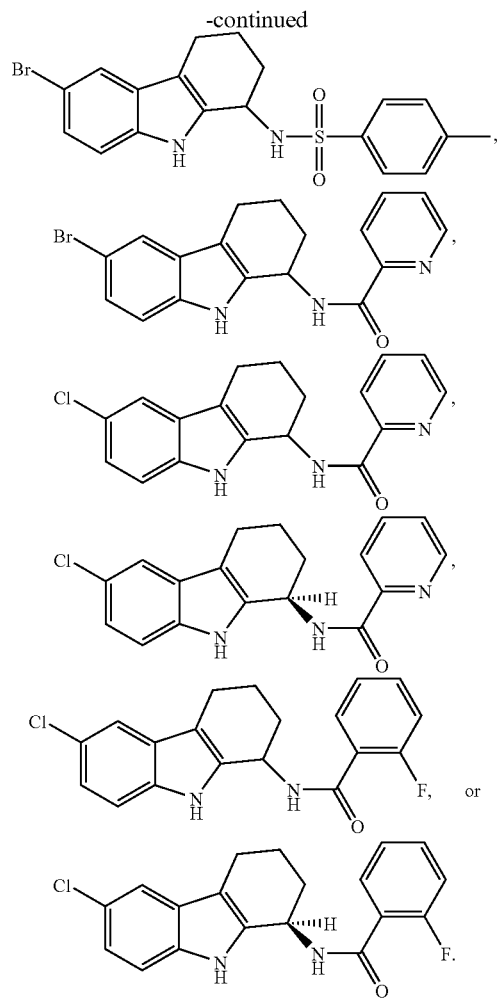

One aspect of the present invention includes one or more of:

N-(6-Bromo-2,3,4,9-tetrahydro-1H-carbazol-1-yl)-N'-phenylurea;

N-(6-Bromo-2,3,4,9-tetrahydro-1H-carbazol-1-yl)-N'-(4-methoxyphenyl)urea;

N-(6-Bromo-2,3,4,9-tetrahydro-1H-carbazol-1-yl)-N'-(4-methoxy-2-methylphenyl)urea;

N-(6-Bromo-2,3,4,9-tetrahydro-1H-carbazol-1-yl)-N'-(3-chloro-4-methoxyphenyl)urea;

N-(6-Bromo-2,3,4,9-tetrahydro-1H-carbazol-1-yl)-N'-[4-(dimethylamino)phenyl]urea;

N-(6-Bromo-2,3,4,9-tetrahydro-1H-carbazol-1-yl)benzamide;

N-[(1R)-6-bromo-2,3,4,9-tetrahydro-1H-carbazol-1-yl]benzamide;

N-[(1S)-6-bromo-2,3,4,9-tetrahydro-1H-carbazol-1-yl]benzamide;

N-(6-Bromo-2,3,4,9-tetrahydro-1H-carbazol-1-yl)-2-phenylacetamide;

N-(6-Bromo-2,3,4,9-tetrahydro-1H-carbazol-1-yl)-3-phenylpropanamide;

N-(6-Bromo-2,3,4,9-tetrahydro-1H-carbazol-1-yl)-3-phenylprop-2-enamide;

Benzyl 6-bromo-2,3,4,9-tetrahydro-1H-carbazol-1-ylcarbamate;

N-(6-Bromo-2,3,4,9-tetrahydro-1H-carbazol-1-yl)-2,6-dichlorobenzamide;
N-(6-Bromo-2,3,4,9-tetrahydro-1H-carbazol-1-yl)$_4$-fluorobenzamide;
N-(6-Bromo-2,3,4,9-tetrahydro-1H-carbazol-1-yl)-4-methoxybenzamide;
N-(6-Bromo-2,3,4,9-tetrahydro-1H-carbazol-1-yl)$_4$-nitrobenzamide;
N-(6-Bromo-2,3,4,9-tetrahydro-1H-carbazol-1-yl)$_4$-chlorobenzamide;
N-(6-Bromo-2,3,4,9-tetrahydro-1H-carbazol-1-yl)-4-methylbenzamide;
N-(6-Bromo-2,3,4,9-tetrahydro-1H-carbazol-1-yl)-4-(trifluoromethyl)benzamide;
N-(6-Bromo-2,3,4,9-tetrahydro-1H-carbazol-1-yl)-3-fluorobenzamide;
N-(6-Bromo-2,3,4,9-tetrahydro-1H-carbazol-1-yl)-3-methoxybenzamide;
N-(6-Bromo-2,3,4,9-tetrahydro-1H-carbazol-1-yl)-3-methylbenzamide;
N-(6-Bromo-2,3,4,9-tetrahydro-1H-carbazol-1-yl)-2-fluorobenzamide;
N-(6-Bromo-2,3,4,9-tetrahydro-1H-carbazol-1-yl)-2-methoxybenzamide;
N-(6-Bromo-2,3,4,9-tetrahydro-1H-carbazol-1-yl)-2-nitrobenzamide;
N-(6-Bromo-2,3,4,9-tetrahydro-1H-carbazol-1-yl)-2-chlorobenzamide;
N-(6-Bromo-2,3,4,9-tetrahydro-1H-carbazol-1-yl)-2-methylbenzamide;
N-(2,3,4,9-Tetrahydro-1H-carbazol-1-yl)benzamide;
N-(6-Methyl-2,3,4,9-tetrahydro-1H-carbazol-1-yl)benzamide;
N-(6-Chloro-2,3,4,9-tetrahydro-1H-carbazol-1-yl)benzamide;
N-[(1R)-6-chloro-2,3,4,9-tetrahydro-1H-carbazol-1-yl]benzamide;
N-[(1S)-6-chloro-2,3,4,9-tetrahydro-1H-carbazol-1-yl]benzamide;
N-(6-Bromo-2,3,4,9-tetrahydro-1H-carbazol-1-yl)$_p$-methylbenzenesulfonamide;
N-(6-Bromo-2,3,4,9-tetrahydro-1H-carbazol-1-yl)pyridine-2-carboxamide;
N-(6-Bromo-2,3,4,9-tetrahydro-1H-carbazol-1-yl) nicotinamide;
N-(6-Bromo-2,3,4,9-tetrahydro-1H-carbazol-1-yl)-6-chloronicotinamide;
N-(6-Bromo-2,3,4,9-tetrahydro-1H-carbazol-1-yl)isonicotinamide;
N-Phenyl-N'-(2,3,4,9-tetrahydro-1H-carbazol-1-yl)urea;
N-(6-Methyl-2,3,4,9-tetrahydro-1H-carbazol-1-yl)-N'-phenylurea;
N-(6-Chloro-2,3,4,9-tetrahydro-1H-carbazol-1-yl)-N'-phenylurea;
N-(6-Chloro-2,3,4,9-tetrahydro-1H-carbazol-1-yl)-2-pyridinecarboxamide;
N-[(1R)-6-chloro-2,3,4,9-tetrahydro-1H-carbazol-1-yl]pyridine-2-carboxamide;
N-[(1S)-6-chloro-2,3,4,9-tetrahydro-1H-carbazol-1-yl]pyridine-2-carboxamide;
N-(6-Bromo-2,3,4,9-tetrahydro-1H-carbazol-1-yl)-2-fluorobenzamide;
N-[(1R)-6-chloro-2,3,4,9-tetrahydro-1H-carbazol-1-yl]-2-fluorobenzamide;
N-[(1S)-6-chloro-2,3,4,9-tetrahydro-1H-carbazol-1-yl]-2-fluorobenzamide;
N-(6-Chloro-2,3,4,9-tetrahydro-1H-carbazol-1-yl)-1-methyl-1H-imidazole-5-carboxamide;
N-(6-Chloro-2,3,4,9-tetrahydro-1H-carbazol-1-yl)-1-methyl-1H-pyrazole-5-carboxamide;
N-(6-Chloro-2,3,4,9-tetrahydro-1H-carbazol-1-yl)-1-methyl-1H-pyrazole-3-carboxamide;
N-(6-Chloro-2,3,4,9-tetrahydro-1H-carbazol-1-yl)-1H-imidazole-4-carboxamide;
N-(6-Chloro-2,3,4,9-tetrahydro-1H-carbazol-1-yl)-1H-pyrazole-3-carboxamide;
N-(6-bromo-2,3,4,9-tetrahydro-1H-carbazol-1-yl)-2,6-difluorobenzamide;
N-(6-bromo-2,3,4,9-tetrahydro-1H-carbazol-1-yl)-2-fluorobenzenesulfonamide; and
N-(6-bromo-2,3,4,9-tetrahydro-1H-carbazol-1-yl)-2,6-difluorobenzenesulfonamide.

Preferably, another aspect includes one or more of:
N-(6-Bromo-2,3,4,9-tetrahydro-1H-carbazol-1-yl)-N'-[4-(dimethylamino)phenyl]urea;
N-(6-Bromo-2,3,4,9-tetrahydro-1H-carbazol-1-yl)benzamide;
N-[(1R)-6-bromo-2,3,4,9-tetrahydro-1H-carbazol-1-yl]benzamide;
N-(6-Bromo-2,3,4,9-tetrahydro-1H-carbazol-1-yl)-3-phenylprop-2-enamide;
Benzyl 6-bromo-2,3,4,9-tetrahydro-1H-carbazol-1-ylcarbamate;
N-(6-Bromo-2,3,4,9-tetrahydro-1H-carbazol-1-yl)-4-fluorobenzamide;
N-(6-Bromo-2,3,4,9-tetrahydro-1H-carbazol-1-yl)-4-methoxybenzamide;
N-(6-Bromo-2,3,4,9-tetrahydro-1H-carbazol-1-yl)-4-nitrobenzamide;
N-(6-Bromo-2,3,4,9-tetrahydro-1H-carbazol-1-yl)$_4$-chlorobenzamide;
N-(6-Bromo-2,3,4,9-tetrahydro-1H-carbazol-1-yl)-4-methylbenzamide;
N-(6-Bromo-2,3,4,9-tetrahydro-1H-carbazol-1-yl)-4-(trifluoromethyl)benzamide;
N-(6-Bromo-2,3,4,9-tetrahydro-1H-carbazol-1-yl)-3-fluorobenzamide;
N-(6-Bromo-2,3,4,9-tetrahydro-1H-carbazol-1-yl)-3-methoxybenzamide;
N-(6-Bromo-2,3,4,9-tetrahydro-1H-carbazol-1-yl)-3-methylbenzamide;
N-(6-Bromo-2,3,4,9-tetrahydro-1H-carbazol-1-yl)-2-fluorobenzamide;
N-(6-Bromo-2,3,4,9-tetrahydro-1H-carbazol-1-yl)-2-methylbenzamide;
N-(6-Methyl-2,3,4,9-tetrahydro-1H-carbazol-1-yl)benzamide;
N-(6-Chloro-2,3,4,9-tetrahydro-1H-carbazol-1-yl)benzamide;
N-[(1R)-6-chloro-2,3,4,9-tetrahydro-1H-carbazol-1-yl]benzamide;
N-(6-Bromo-2,3,4,9-tetrahydro-1H-carbazol-1-yl)-4-methylbenzenesulfonamide;
N-(6-Bromo-2,3,4,9-tetrahydro-1H-carbazol-1-yl)pyridine-2-carboxamide;
N-(6-Bromo-2,3,4,9-tetrahydro-1H-carbazol-1-yl)nicotinamide;
N-(6-Bromo-2,3,4,9-tetrahydro-1H-carbazol-1-yl)-6-chloronicotinamide;
N-(6-Bromo-2,3,4,9-tetrahydro-1H-carbazol-1-yl)isonicotinamide;
N-(6-Chloro-2,3,4,9-tetrahydro-1H-carbazol-1-yl)-2-pyridinecarboxamide;

N-[(1R)-6-chloro-2,3,4,9-tetrahydro-1H-carbazol-1-yl]pyridine-2-carboxamide;
N-(6-Chloro-2,3,4,9-tetrahydro-1H-carbazol-1-yl)-2-fluorobenzamide;
N-[(1R)-6-chloro-2,3,4,9-tetrahydro-1H-carbazol-1-yl]-2-fluorobenzamide;
N-[(1R)-6-chloro-2,3,4,9-tetrahydro-1H-carbazol-1-yl]-2-fluorobenzamide;
N-(6-Chloro-2,3,4,9-tetrahydro-1H-carbazol-1-yl)-1H-imidazole-4-carboxamide;
N-(6-Chloro-2,3,4,9-tetrahydro-1H-carbazol-1-yl)-1H-pyrazole-3-carboxamide;
N-(6-bromo-2,3,4,9-tetrahydro-1H-carbazol-1-yl)-2,6-difluorobenzamide;
N-(6-bromo-2,3,4,9-tetrahydro-1H-carbazol-1-yl)-2-fluorobenzenesulfonamide; and
N-(6-bromo-2,3,4,9-tetrahydro-1H-carbazol-1-yl)-2,6-difluorobenzenesulfonamide.

More preferably, one aspect includes one or more of:
N-(6-Bromo-2,3,4,9-tetrahydro-1H-carbazol-1-yl)benzamide;
N-[(1R)-6-bromo-2,3,4,9-tetrahydro-1H-carbazol-1-yl]benzamide;
Benzyl 6-bromo-2,3,4,9-tetrahydro-1H-carbazol-1-ylcarbamate;
N-(6-Bromo-2,3,4,9-tetrahydro-1H-carbazol-1-yl)$_4$-fluorobenzamide;
N-(6-Bromo-2,3,4,9-tetrahydro-1H-carbazol-1-yl)-4-methoxybenzamide;
N-(6-Bromo-2,3,4,9-tetrahydro-1H-carbazol-1-yl)$_4$-nitrobenzamide;
N-(6-Bromo-2,3,4,9-tetrahydro-1H-carbazol-1-yl)$_4$-chlorobenzamide;
N-(6-Bromo-2,3,4,9-tetrahydro-1H-carbazol-1-yl)$_4$-methylbenzamide;
N-(6-Bromo-2,3,4,9-tetrahydro-1H-carbazol-1-yl)-3-fluorobenzamide;
N-(6-Bromo-2,3,4,9-tetrahydro-1H-carbazol-1-yl)-3-methoxybenzamide;
N-(6-Bromo-2,3,4,9-tetrahydro-1H-carbazol-1-yl)-3-methylbenzamide;
N-(6-Bromo-2,3,4,9-tetrahydro-1H-carbazol-1-yl)-2-fluorobenzamide;
N-(6-chloro-2,3,4,9-tetrahydro-1H-carbazol-1-yl)benzamide;
N-[(1R)-6-chloro-2,3,4,9-tetrahydro-1H-carbazol-1-yl]benzamide;
N-(6-Bromo-2,3,4,9-tetrahydro-1H-carbazol-1-yl)$_4$-methylbenzenesulfonamide;
N-(6-Bromo-2,3,4,9-tetrahydro-1H-carbazol-1-yl)pyridine-2-carboxamide;
N-(6-Bromo-2,3,4,9-tetrahydro-1H-carbazol-1-yl)-6-chloronicotinamide;
N-(6-Chloro-2,3,4,9-tetrahydro-1H-carbazol-1-yl)-2-pyridinecarboxamide;
N-[(1R)-6-chloro-2,3,4,9-tetrahydro-1H-carbazol-1-yl]pyridine-2-carboxamide;
N-(6-Chloro-2,3,4,9-tetrahydro-1H-carbazol-1-yl)-2-fluorobenzamide;
N-[(1R)-6-chloro-2,3,4,9-tetrahydro-1H-carbazol-1-yl]-2-fluorobenzamide;
N-(6-bromo-2,3,4,9-tetrahydro-1H-carbazol-1-yl)-2,6-difluorobenzamide; and
N-(6-bromo-2,3,4,9-tetrahydro-1H-carbazol-1-yl)-2-fluorobenzenesulfonamide.

Another embodiment of the present invention includes:

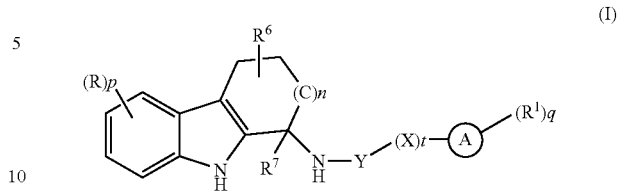

(I)

including salts, solvates and pharmaceutically functional derivatives wherein $R^6$ is H, alkyl, —$OR^2$, —$NR^2R^3$, Ay, Het, —$C(O)R^2$, —$CO_2R^2$, —$CONR^2R^3$, —$S(O)_mR^2$, or oxo, where the variables are as defined above; and $R^7$ is H or alkyl; provided $R^6$ and $R^7$ are not both H.

One aspect of the present invention includes a pharmaceutical composition comprising a compound of the present invention and a pharmaceutically acceptable carrier.

One aspect of the present invention includes a compound of the present invention for use as an active therapeutic substance.

One aspect of the present invention includes a compound of the present invention for use in the treatment or prophylaxis of diseases and conditions caused by oncogenic viruses, including adenoviruses, retroviruses, and papovavirus family, including polyoma viruses and papilloma viruses.

One aspect of the present invention includes a compound of the present invention for use in the treatment or prophylaxis of conditions or disorders due to HPV infection. Particularly the condition or disease is warts, genital warts, cervical dysplasia, recurrent respiratory papillomatosis, or cancers associated with papillomavirus infection. More particularly the cancer is anogenital cancers, head and neck cancers, and skin cancers. More particularly the anogenital cancers are cervical, anal and perianal, vulvar, vaginal, and penile cancers; the head and neck cancers are oral pharyngeal region and esophagus cancers; and the skin cancers are basal cell carcinoma and squamous cell carcinoma.

Another aspect of the present invention also includes the use of a compound of the present invention in the manufacture of a medicament for use in the treatment or prophylaxis of oncogenic viruses, including adenoviruses, retroviruses, and papovavirus family, including polyoma viruses and papilloma viruses.

One aspect of the present invention includes the use of a compound of the present invention in the manufacture of a medicament for use in the treatment or prophylaxis of conditions or disorders due to HPV infection. Particularly the present invention includes usefulness with regard to warts, genital warts, cervical dysplasia, recurrent respiratory papillomatosis, or cancers associated with papillomavirus infection.

One aspect of the present invention includes a method for the treatment or prophylaxis of oncogenic viruses, including adenoviruses, retroviruses, and papovavirus family, including polyoma viruses and papilloma viruses comprising the administration of a compound according to the present invention.

One aspect of the present invention includes a method for the treatment or prophylaxis of conditions or disorders due to HPV infection comprising the administration of a compound according to the present invention. Particularly the condition or disorder is warts, genital warts, cervical dysplasia, recurrent respiratory papillomatosis, or cancers associated with papillomavirus infection.

As noted herein, p and q are each independently defined as 0, 1, 2, 3, 4, or 5. Notably, as will be appreciated by those skilled in the art, the value(s) of p and/or q should not exceed the substitutable positions on the depicted rings.

DETAILED DESCRIPTION OF THE PREFERRED EMBODIMENT

Terms are used within their accepted meanings. The following definitions are meant to clarify, but not limit, the terms defined.

As used herein the term "alkyl" refers to a straight or branched chain hydrocarbon, preferably having from one to twelve carbon atoms, that may be optionally substituted, with multiple degrees of substitution included within the present invention. Examples of "alkyl" as used herein include, but are not limited to, methyl, ethyl, propyl, isopropyl, isobutyl, n-butyl, tert-butyl, isopentyl, n-pentyl, and substituted versions thereof.

As used throughout this specification, the preferred number of atoms, such as carbon atoms, will be represented by, for example, the phrase "$C_x$-$C_y$ alkyl," which refers to an alkyl group, as herein defined, containing the specified number of carbon atoms. Similar terminology will apply for other preferred terms and ranges as well.

As used herein the term "alkenyl" refers to a straight or branched chain aliphatic hydrocarbon containing one or more carbon-to-carbon double bonds that may be optionally substituted, with multiple degrees of substitution included within the present invention. Examples include, but are not limited to, vinyl, allyl, and the like and substituted versions thereof.

As used herein the term "alkynyl" refers to a straight or branched chain aliphatic hydrocarbon containing one or more carbon-to-carbon triple bonds that may be optionally substituted, with multiple degrees of substitution included within the present invention. Examples include, but are not limited to, ethynyl and the like and substituted versions thereof.

As used herein, the term "alkylene" refers to a straight or branched chain divalent hydrocarbon radical, preferably having from one to ten carbon atoms. Alkylene groups as defined herein may optionally be substituted, with multiple degrees of substitution included within the present invention. Examples of "alkylene" as used herein include, but are not limited to, methylene, ethylene, n-propylene, n-butylene, and substituted versions thereof.

As used herein, the term "alkenylene" refers to a straight or branched chain divalent hydrocarbon radical, preferably having from one to ten carbon atoms, containing one or more carbon-to-carbon double bonds that may be optionally substituted, with multiple degrees of substitution included within the present invention. Examples include, but are not limited to, vinylene, allylene or 2-propenylene, and the like and substituted versions thereof.

As used herein, the term "alkynylene" refers to a straight or branched chain divalent hydrocarbon radical, preferably having from one to ten carbon atoms, containing one or more carbon-to-carbon triple bonds that may be optionally substituted, with multiple degrees of substitution included within the present invention. Examples include, but are not limited to, ethynylene and the like and substituted versions thereof.

As used herein, the term "cycloalkyl" refers to an optionally substituted non-aromatic cyclic hydrocarbon ring, which optionally includes an alkylene linker through which the cycloalkyl may be attached, with multiple degrees of substitution included within the present invention. Exemplary "cycloalkyl" groups include, but are not limited to, cyclopropyl, cyclobutyl, cyclopentyl, cyclohexyl, cycloheptyl, and substituted versions thereof. As used herein, the term "cycloalkyl" includes an optionally substituted fused polycyclic hydrocarbon saturated ring and aromatic ring system, namely polycyclic hydrocarbons with less than maximum number of non-cumulative double bonds, for example where a saturated hydrocarbon ring (such as a cyclopentyl ring) is fused with an aromatic ring (herein "aryl," such as a benzene ring) to form, for example, groups such as indane.

As used herein, the term "cycloalkenyl" refers to an optionally substituted non-aromatic cyclic hydrocarbon ring containing one or more carbon-to-carbon double bonds which optionally includes an alkylene linker through which the cycloalkenyl may be attached, with multiple degrees of substitution included within the present invention. Exemplary "cycloalkenyl" groups include, but are not limited to, cyclopropenyl, cyclobutenyl, cyclopentenyl, cyclohexenyl, cycloheptenyl, and substituted versions thereof.

As used herein, the term "cycloalkylene" refers to a divalent, optionally substituted non-aromatic cyclic hydrocarbon ring, with multiple degrees of substitution included within the present invention. Exemplary "cycloalkylene" groups include, but are not limited to, cyclopropylene, cyclobutylene, cyclopentylene, cyclohexylene, cycloheptylene, and substituted versions thereof.

As used herein, the term "cycloalkenylene" refers to a divalent optionally substituted non-aromatic cyclic hydrocarbon ring containing one or more carbon-to-carbon double bonds, with multiple degrees of substitution included within the present invention. Exemplary "cycloalkenylene" groups include, but are not limited to, cyclopropenylene, cyclobutenylene, cyclopentenylene, cyclohexenylene, cycloheptenylene, and substituted versions thereof.

As used herein, the term "heterocycle" or "heterocyclyl" refers to an optionally substituted mono- or polycyclic ring system containing one or more degrees of unsaturation and also containing one or more heteroatoms. Preferred heteroatoms include N, O, and/or S, including N-oxides, sulfur oxides, and dioxides. Preferably the ring is three to twelve-membered and is either fully saturated or has one or more degrees of unsaturation. Multiple degrees of substitution are included within the present definition. Such rings may be optionally fused to one or more of another "heterocyclic" ring(s) or cycloalkyl ring(s). Examples of "heterocyclic" groups include, but are not limited to, tetrahydrofuran, pyran, 1,4-dioxane, 1,3-dioxane, piperidine, pyrrolidine, morpholine, tetrahydrothiopyran, and tetrahydrothiophene.

As used herein, the term "aryl" refers to an optionally substituted benzene ring or to an optionally substituted fused benzene ring system, for example anthracene, phenanthrene, or naphthalene ring systems. Multiple degrees of substitution are included within the present definiton. Examples of "aryl" groups include, but are not limited to, phenyl, 2-naphthyl, 1-naphthyl, and substituted derivatives thereof.

As used herein, the term "heteroaryl" refers to an optionally substituted monocyclic five to seven membered aromatic ring, or to an optionally substituted fused bicyclic aromatic ring system comprising two of such aromatic rings. These heteroaryl rings contain one or more nitrogen, sulfur, and/or oxygen atoms, where N-oxides, sulfur oxides, and dioxides are permissible heteroatom substitutions. Multiple degrees of substitution are included within the present definition. Examples of "heteroaryl" groups used herein include, but should not be limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, benzimidizolyl, imidazopyridinyl, pyrazolopyridinyl, pyrazolopyrimidinyl, and substituted versions thereof.

As used herein the term "halogen" refers to fluorine, chlorine, bromine, or iodine.

As used herein the term "haloalkyl" refers to an alkyl group, as defined herein, that is substituted with at least one halogen. Examples of branched or straight chained "haloalkyl" groups useful in the present invention include, but are not limited to, methyl, ethyl, propyl, isopropyl, n-butyl, and t-butyl substituted independently with one or more halogens, e.g., fluoro, chloro, bromo, and iodo. The term "haloalkyl" should be interpreted to include such substituents as perfluoroalkyl groups and the like.

As used herein the term "alkoxy" refers to the group —OR$^a$, where R$^a$ is alkyl as defined above.

As used herein the term "alkoxycarbonyl" refers to groups such as:

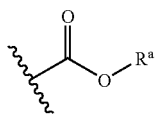

where the R$^a$ represents an alkyl group as herein defined.

As used herein the term "aryloxycarbonyl" refers to groups such as:

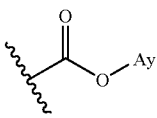

where the Ay represents an aryl group as herein defined.

As used herein the term "heteroaryloxycarbonyl" refers to groups such as:

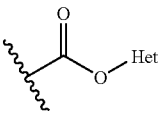

where the Het represents a heteroaryl group as herein defined.

As used herein the term "nitro" refers to the group —NO$_2$.

As used herein the term "cyano" refers to the group —CN.

As used herein the term "azido" refers to the group —N$_3$.

As used herein the term "acyl" refers to the group R$^b$C(O)—, where R$^b$ is alkyl, aryl, heteroaryl, or heterocyclyl, as each is defined herein.

As used herein the term "oxo" refers to the group =O.

Also, as used herein throughout the present specification, the phrase "optionally substituted" or variations thereof denote an optional substitution, including multiple degrees of substitution, with one or more substitutent group. The phrase should not be interpreted as duplicative of the substitutions herein described and depicted. Exemplary optional substituent groups include acyl; alkyl; alkenyl; alkynyl; alkylsulfonyl; alkoxy; alkoxycarbonyl; cyano; halogen; haloalkyl; hydroxy; nitro; aryl, which may be further substituted with acyl, alkoxy, alkyl, alkenyl, alkynyl, alkylsulfonyl, cyano, halogen, haloalkyl, hydroxy, or nitro; heteroaryl, which may be further substituted with acyl, alkoxy, alkyl, alkenyl, alkynyl, alkylsulfonyl, cyano, halogen, haloalkyl, hydroxy, or nitro; arylsulfonyl, which may be further substituted with acyl, alkoxy, alkyl, alkenyl, alkynyl, alkylsulfonyl, cyano, halogen, haloalkyl, hydroxy, or nitro; heteroarylsulfonyl, which may be further substituted with acyl, alkoxy, alkyl, alkenyl, alkynyl, alkylsulfonyl, cyano, halogen, haloalkyl, hydroxy, or nitro; aryloxy, which may be further substituted with acyl, alkoxy, alkyl, alkenyl, alkynyl, alkylsulfonyl, cyano, halogen, haloalkyl, hydroxy, or nitro; heteroaryloxy, which may be further substituted with acyl, alkoxy, alkyl, alkenyl, alkynyl, alkylsulfonyl, cyano, halogen, haloalkyl, hydroxy, or nitro; aryloxycarbonyl, which may be further substituted with acyl, alkoxy, alkyl, alkenyl, alkynyl, alkylsulfonyl, cyano, halogen, haloalkyl, hydroxy, or nitro; heteroaryloxycarbonyl, which may be further substituted with acyl, alkoxy, alkyl, alkenyl, alkynyl, alkylsulfonyl, cyano, halogen, haloalkyl, hydroxy, or nitro; or —N(R*)$_2$; where for each occurrence R* is independently selected from H, alkyl, alkenyl, alkynyl, cycloalkyl, heterocyclyl, aryl, aralkyl, heteroaryl, heteroaralkyl, alkylsulfonyl, arylsulfonyl, or heteroarylsulfonyl, where each occurrence of such aryl or heteroaryl may be substituted with one or more acyl, alkoxy, alkyl, alkenyl, alkylsulfonyl, cyano, halogen, haloalkyl, hydroxy, or nitro, or the two R*s may combine to form a ring, optionally having additional heteroatoms, optionally having one or more degrees of unsaturation, and optionally being further substituted with acyl, alkoxy, alkyl, alkenyl, alkynyl, alkylsulfonyl, cyano, halogen, haloalkyl, hydroxy, or nitro.

The compounds of formulas (I) may crystallize in more than one form, a characteristic known as polymorphism, and such polymorphic forms ("polymorphs") are within the scope of formula (I). Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by formula (I), as well as any wholly or partially equilibrated mixtures thereof. The present invention also includes the individual isomers of the compounds represented by the formulas above as mixtures with isomers thereof in which one or more chiral centers are inverted.

Typically, but not absolutely, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts. Representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts. Other salts, which are not pharmaceutically acceptable, may be useful in the preparation of compounds of this invention and these should be considered to form a further aspect of the invention.

As used herein, the term "solvate" refers to a complex of variable stoichiometry formed by a solute (in this invention, a compound of Formula I, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid. Most preferably the solvent used is water.

As used herein, the term "physiologically functional derivative" refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art, without undue experimentation. Reference may be made to the teaching of *Burger's Medicinal Chemistry And Drug Discovery,* $5^{th}$ Edition, Vol 1: Principles and Practice, which is incorporated herein by reference to the extent that it teaches physiologically functional derivatives.

As used herein, the term "effective amount" means that amount of a drug or pharmaceutical agent that will elicit the biological or medical response of a tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of formula (I), as well as salts, solvates, and physiological functional derivatives thereof, may be administered as the raw chemical. Additionally, the active ingredient may be presented as a pharmaceutical composition.

Accordingly, the invention further provides pharmaceutical compositions that include effective amounts of compounds of the formula (I) and salts, solvates, and physiological functional derivatives thereof, and one or more pharmaceutically acceptable carriers, diluents, or excipients. The compounds of formula (I) and salts, solvates, and physiologically functional derivatives thereof, are as herein described. The carrier(s), diluent(s) or excipient(s) must be acceptable, in the sense of being compatible with the other ingredients of the formulation and not deleterious to the recipient of the pharmaceutical composition.

In accordance with another aspect of the invention there is also provided a process for the preparation of a pharmaceutical formulation including admixing a compound of the formula (I) or salts, solvates, and physiological functional derivatives thereof, with one or more pharmaceutically acceptable carriers, diluents or excipients.

A therapeutically effective amount of a compound of the present invention will depend upon a number of factors. For example, the species, age, and weight of the recipient, the precise condition requiring treatment and its severity, the nature of the formulation, and the route of administration are all factors to be considered. The therapeutically effective amount ultimately should be at the discretion of the attendant physician or veterinarian. Regardless, an effective amount of a compound of formula (I) for the treatment of humans suffering from frailty, generally, should be in the range of 0.1 to 100 mg/kg body weight of recipient (mammal) per day. More usually the effective amount should be in the range of 1 to 10 mg/kg body weight per day. Thus, for a 70 kg adult mammal the actual amount per day would usually be from 70 to 700 mg. This amount may be given in a single dose per day or in a number (such as two, three, four, five, or more) of sub-doses per day such that the total daily dose is the same. An effective amount of a salt, solvate, or physiologically functional derivative thereof, may be determined as a proportion of the effective amount of the compound of formula (I) per se. Similar dosages should be appropriate for treatment of the other conditions referred to herein.

Pharmaceutical formulations may be presented in unit dose forms containing a predetermined amount of active ingredient per unit dose. Such a unit may contain, as a non-limiting example, 0.5 mg to 1 g of a compound of the formula (I), depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s). By way of example, and not meant to limit the invention, with regard to certain conditions and disorders for which the compounds of the present invention are believed useful certain routes will be preferable to others. Based upon the physical manifestations that are often associated with HPV infection, rectal, topical, or vaginal routes of administration may be preferable. As one example, for the treatment or prophylaxis of cervical dysplasia the preferred route may be a vaginal route.

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate, or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I) and salts, solvates, and physiological functional derivatives thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula (I) and salts, solvates, and physiologically functional derivatives thereof may also be delivered by the use of monoclonal antibodies as individual carriers to which the compound molecules are coupled.

The compounds may also be coupled with soluble polymers as targetable drug carriers. Such polymers can include polyvinylpyrrolidone (PVP), pyran copolymer, polyhydroxypropylmethacrylamide-phenol, polyhydroxyethyl-aspartamidephenol, or polyethyleneoxidepolylysine substituted with palmitoyl residues. Furthermore, the compounds may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6), 318 (1986), incorporated herein by reference as related to such delivery systems.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, nebulizers, or insufflators.

Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring or coloring agents.

The compounds of the present invention and their salts, solvates, and physiologically functional derivatives thereof, may be employed alone or in combination with other therapeutic agents. The compound(s) of formula (I) and the other pharmaceutically active agent(s) may be administered together or separately and, when administered separately, administration may occur simultaneously or sequentially, in any order. The amounts of the compound(s) of formula (I) and the other pharmaceutically active agent(s) and the relative timings of administration will be selected in order to achieve the desired combined therapeutic effect. The administration in combination of a compound of formula (I) salts, solvates, or physiologically functional derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

The compounds of the present invention may be used in the treatment of a variety of disorders and conditions and, as such, the compounds of the present invention may be used in combination with a variety of other suitable therapeutic agents useful in the treatment or prophylaxis of those disorders or conditions. Treatment will depend upon the nature and type of HPV infection. As discussed briefly above, treatment for warts can be divided into ablative and medical approaches. The compounds of the present invention may be combined with either or both approaches.

Ablative methods include classic surgical excision and destruction by electrodesiccation, laser, or liquid nitrogen. Thus, the compounds of the present invention may be used in conjunction with such methods or upon reoccurrence after such methods. The compounds of the present invention may be used in conjunction with ablative methods to reduce the frequency of reoccurrence.

Alternatively, the present invention may be combined with other medical therapies including a variety of cytotoxic or antiviral agents. For example, and not meant to limit the invention, the compounds of the present invention may be combined with other therapeutic agents such as 5-fluorouracil, retinoic acid, podophyllin, podofilox, keratolytic agents such as salicylic acid and/or lactic acid, haptens such as diphencyprone (DPC), squaric acid dibutyl ester (SADBE) or dinitrochlorobenzene (DNCB), formalin, topical trichloroacetic acid, topical tretinoin, cidofovir, resiquimod and/or cytokines such as interferon alfa-2b.

One aspect of the present invention is the use of the compounds of the present invention for the treatment or prophylaxis of a variety of disorders including, but not limited to, diseases and conditions caused by oncogenic viruses, including adenoviruses, retroviruses, and papovavirus family, including polyoma viruses and papilloma viruses and more particularly papilloma viral infections. The present invention includes administering to a subject in need thereof a therapeutically effective amount of a compound of the present invention or a pharmaceutically acceptable salt, solvate or physiologically functional derivative thereof.

More specifically, the present invention includes the treatment or prophylaxis of conditions or diseases associated with papilloma viral infections. These conditions and diseases include warts (e.g. plantar warts), genital warts, recurrent respiratory papillomatosis (e.g., laryngeal papillomas), and cancers associated with papillomavirus infection. Cancers that have been associated with papillomavirus infection include anogenital cancers (e.g., cervical, anal and perianal, vulvar, vaginal, penile cancers), head and neck cancers (e.g., oral pharyngeal region, esophagus), and skin cancers (e.g., basal cell carcinoma, squamous cell carcinoma). The present invention includes administering to a subject in need thereof a therapeutically effective amount of a compound of the present invention or a salt, solvate or physiologically functional derivative thereof.

The compounds of this invention may be made by a variety of methods, including well-known standard synthetic methods. Illustrative general synthetic methods are set out below and then specific compounds of the invention are prepared in the working Examples.

In all of the examples described below, protecting groups for sensitive or reactive groups are employed where necessary in accordance with general principles of synthetic chemistry. Protecting groups are manipulated according to standard methods of organic synthesis (T. W. Green and P. G. M. Wuts (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of formula (I).

Those skilled in the art will recognize if a stereocenter exists in compounds of formula (I). Accordingly, the present invention includes all possible stereoisomers and includes not only racemic compounds but the individual enantiomers as well. When a compound is desired as a single enantiomer, such may be obtained by stereospecific synthesis, by resolution of the final product or any convenient intermediate, or by chiral chromatographic methods as are known in the art. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994), incorporated by reference with regard to stereochemistry.

EXPERIMENTAL SECTION

Abbreviations:

As used herein the symbols and conventions used in these processes, schemes and examples are consistent with those used in the contemporary scientific literature, for example, the Journal of the American Chemical Society or the Journal of Biological Chemistry. Specifically, the following abbreviations may be used in the examples and throughout the specification:

g (grams); mg (milligrams);
L (liters); mL (milliliters);

-continued

| | |
|---|---|
| μL (microliters); | psi (pounds per square inch); |
| M (molar); | mM (millimolar); |
| Hz (Hertz); | MHz (megahertz); |
| mol (moles); | mmol (millimoles); |
| RT (room temperature); | h (hours); |
| min (minutes); | TLC (thin layer chromatography); |
| mp (melting point); | RP (reverse phase); |
| Tr (retention time); | TFA (trifluoroacetic acid); |
| TEA (triethylamine); | THF (tetrahydrofuran); |
| TFAA (trifluoroacetic anhydride); | CD3OD (deuterated methanol); |
| CDCl3 (deuterated chloroform); | DMSO (dimethylsulfoxide); |
| SiO2 (silica); | atm (atmosphere); |
| EtOAc (ethyl acetate); | CHCl3 (chloroform); |
| HCl (hydrochloric acid); | Ac (acetyl); |
| DMF (N,N-dimethylformamide); | Me (methyl); |
| Cs2CO3 (cesium carbonate); | EtOH (ethanol); |
| Et (ethyl); | tBu (tert-butyl); |
| MeOH (methanol). | |

Unless otherwise indicated, all temperatures are expressed in ° C. (degrees Centigrade). All reactions conducted at room temperature unless otherwise noted.

$^1$H-NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), or br (broad).

Mass spectra were obtained on Micromass Platform or ZMD mass spectrometers from Micromass Ltd., Altricham, UK, using either Atmospheric Chemical Ionization (APCI) or Electrospray Ionization (ESI).

Analytical thin layer chromatography was used to verify the purity of intermediate(s) which could not be isolated or which were too unstable for full characterization as well as to follow the progress of reaction(s).

The absolute configuration of compounds were assigned by Ab Initio Vibrational Circular Dichroism (VCD) Spectroscopy. The experimental VCD spectrum were acquired in CDCl$_3$ using a Bomem ChirallRTM VCD spectrometer operating between 2000 and 800 cm$^{-1}$. The Gaussian 98 Suite of computational programs was used to calculate model VCD spectrums. The stereochemical assignments were made by comparing this experimental spectrum to the VCD spectrum calculated for a model structure with (R)- or (S)-configuration.

Incorporated by reference with regard to such spectroscopy are: J. R. Chesseman, M. J. Frisch, F. J. Devlin and P. J. Stephens, *Chem. Phys. Lett.* 252 (1996) 211; P. J. Stephens and F. J. Devlin, *Chirality* 12 (2000) 172; and *Gaussian* 98, Revision A.11.4, M. J. Frisch et al., Gaussian, Inc., Pittsburgh Pa., 2002.

Compounds of formula (I) wherein variables are as defined above and LV is a leaving group, namely halogen (F, Cl, Br, I), may be conveniently prepared by the process outlined in Scheme 1 below:

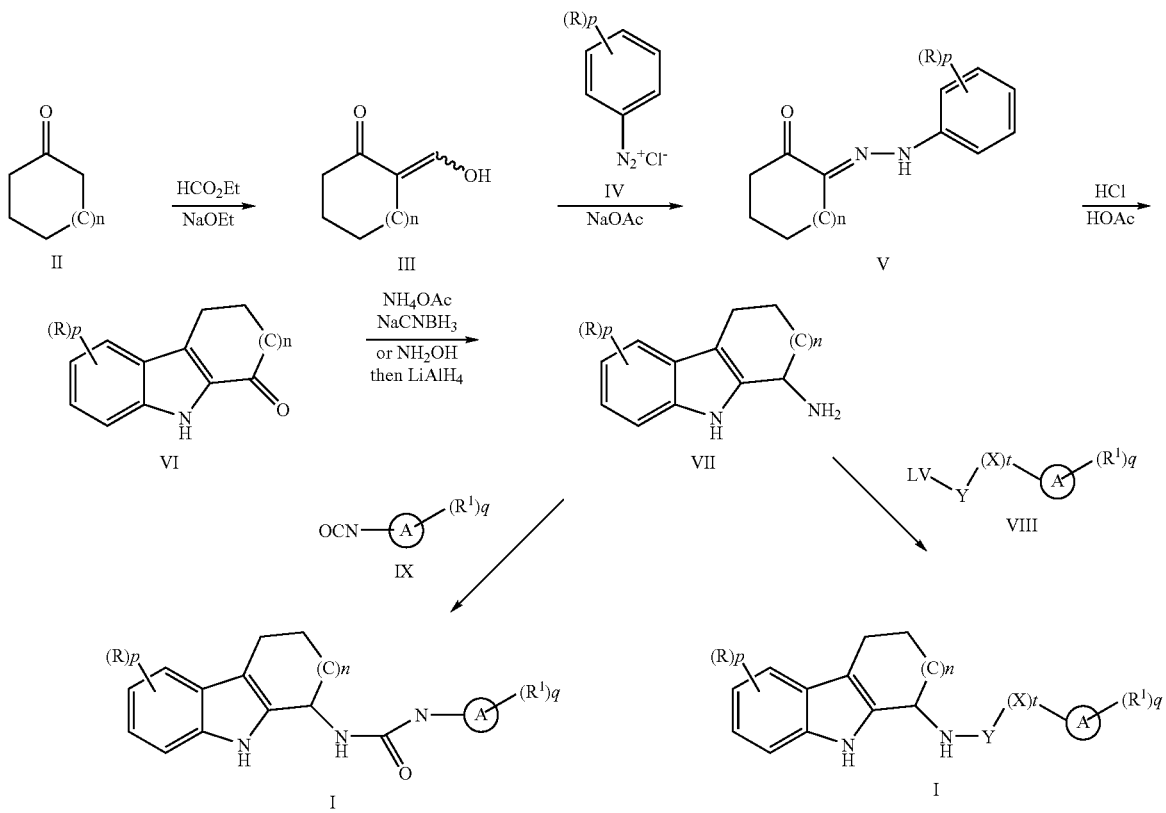

Generally, the process for preparing the compounds of formula (I), where LV is a leaving group as defined above (all formulas and variables as defined above) comprises the steps of:
a) reacting a compound of formula (II) with ethyl formate;
b) reacting the compound of formula (III) with diazacompound of formula (IV);
c) indolizing the compound of formula (V) to prepare a compound of formula (VI);
d) reductive amination of compound of formula (VI) to form compound of formula (VII); and
e) forming compounds of formula (I) from compound (VII) by reaction with compound of formula (VIII); or alternatively
f) forming compounds of formula (I) where Y is CO and X is NH via reaction of compound of formula (VII) with compound of formula (IX).

More specifically, a compound of formula (I) wherein all variables are as defined above can be prepared reacting the compound of formula (VII) with a compound of formula (VIII):

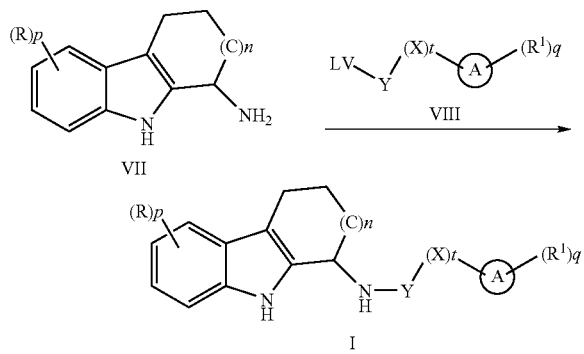

The reaction may be carried out by adding compound of formula (VIII) to a compound of formula (VII) in a suitable solvent, optionally in the presence of base, and optionally with heating. Suitable solvents include tetrahydrofuran, dichloromethane, N,N-dimethylformamide, pyridine, dioxane, diethyl ether, acetonitrile, toluene, and the like. Suitable bases include triethylamine, diisopropylethylamine, pyridine, dimethylaminopyridine, and the like. As will be appreciated by those skilled in the art, compounds of formula (VIII) are commercially available or can be prepared according to literature methods.

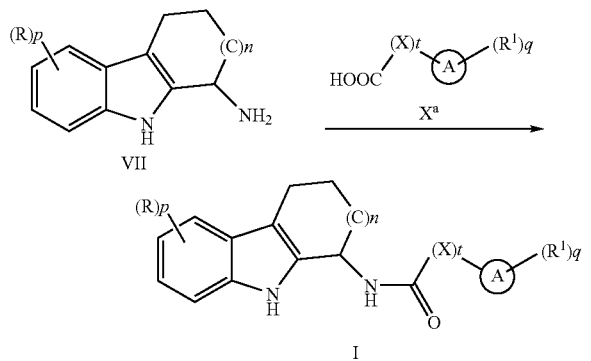

Additionally, as will be appreciated by those skilled in the art, a compound of formula (I) where Y is —C(O)— can also be formed by coupling an amine of formula (VII) and an acid of formula ($X^a$). Any set of standard coupling conditions as are known to those skilled in the art may be used for this coupling.

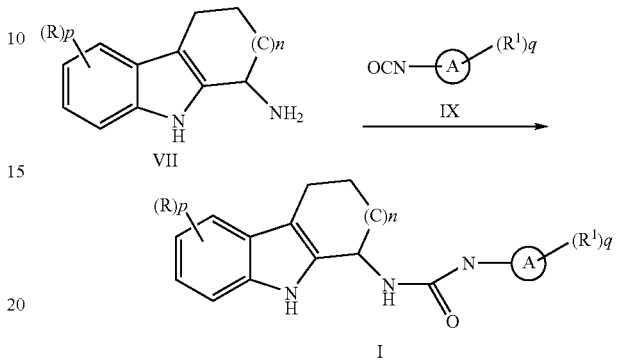

Alternatively, a compound of formula (I) where Y is —CO— and X is —NH— can be formed by the treatment of a compound of formula (VII) with an isocyanate compound of formula (IX) in a suitable solvent, optionally with heating. Suitable solvents include tetrahydrofuran and the like. Isocyanates of formula (IX) are commercially available or may be prepared by literature methods that are appreciated by those skilled in the art.

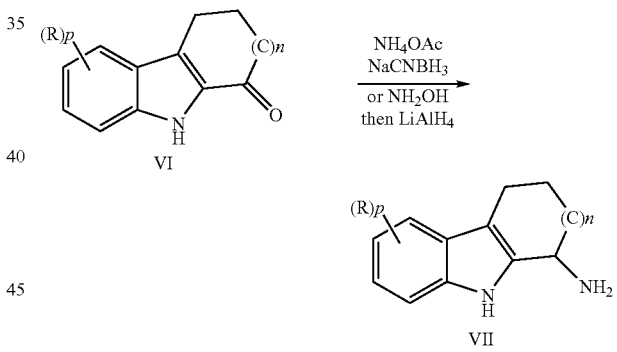

An amine compound of formula (VII) can be formed from a compound of formula (VI). Treatment of a compound of formula (VI) in an inert solvent with ammonium salt and a reductive agent, optionally with heating, gives an amine of formula (VII). Suitable solvents include but are not limited to, methanol, ethanol, dichloromethane, dichloroethane, and the like. Suitable reductive agents include but are not limited to sodium cyanoborohydride, sodium triacetoxyborohydride, sodium borohydride, and the like. Suitable ammonium salts include but are not limited to ammonium acetate, ammonium formate and the like.

An amine of formula (VII) can also be formed by treatment of a compound of formula (VI) with hydroxylamine, followed by reduction with suitable reductive agents which include, but are not limited to, lithium aluminium hydride and the like.

Compounds of formula (VI) are prepared in a similar fashion as described in the literature (J. Med. Chem. 1973, 16, 425 and J. Org. Chem. 1968, 32, 1265), herein incorporated by reference to the extent of such teaching.

A compound of formula (I) can be converted to another compound of formula (I) by methods appreciated by those skilled in the art.

EXAMPLES

Example 1

6-Chloro-2,3,4,9-tetrahydro-1H-carbazol-1-one

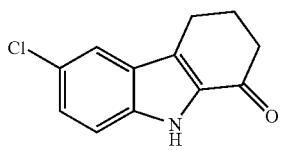

a) Cyclohexane-1,2-dione (4-chlorophenyl)hydrazone

To a cold (0° C.) solution of 4-chloroaniline (5.6 g, 44 mmol) in concentrated hydrochloric acid (5 mL) was added sodium nitrite (3.0 g, 44 mmol) dissolved in water (10 mL) portionwise over 20 minutes. The mixture was stirred at 0° C. for 30 minutes. In a separate flask, a cool solution of 2-(hydroxymethylene)cyclohexanone (Organic Syntheses, Collective Vol 4, 1963, pg. 536) (5.0 g, 40 mmol) in methanol (30 mL) was treated with a solution of sodium acetate (8.3 g, 101 mmol) in water (25 mL). The mixture was stirred at 0° C. for 20 minutes and the diazonium salt slurry was added. The combined mixture was stirred for 10-15 minutes, collected by filtration, triturated with ethanol, and collected by filtration to give cyclohexane-1,2-dione (4-chlorophenyl)hydrazone (4.6 g, 49% yield) as a yellow solid. $^1$H-NMR (DMSO-$d_6$): δ 9.93 (s, 1H), 7.29 (m, 4H), 2.55 (m, 2H), 2.40 (m, 2H), 1.84-1.75 (m, 4H).

b) 6-Chloro-2,3,4,9-tetrahydro-1H-carbazol-1-one

A solution of cyclohexane-1,2-dione (4-chlorophenyl)hydrazone (2.3 g, 9.7 mmol) in hydrochloric acid (2 mL) and acetic acid (8 mL) was heated at 120° C. for 20 minutes. The mixture was cooled slightly and treated with ice water. The resulting precipitate was collected by filtration to give 6-chloro-2,3,4,9-tetrahydro-1H-carbazol-1-one (1.9 g, 88% yield) as brown solid. $^1$H-NMR (DMSO-$d_6$): δ 11.78 (s, 1H), 7.75 (m, 1H), 7.38 (d, 1H), 7.28 (dd, 1H), 2.92 (t, 2H), 2.55 (t, 2H), 2.13 (q, 2H); MS m/z 220 (M+1).

Example 2

6-Chloro-2,3,4,9-tetrahydro-1H-carbazol-1-amine

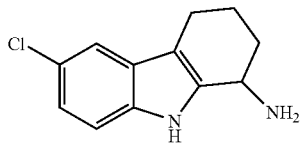

To a solution of 6-chloro-2,3,4,9-tetrahydro-1H-carbazol-1-one (500 mg, 2.3 mmol) and ammonium acetate (1.8 g, 23 mmol) in methanol (9 mL) was added sodium cyanoborohydride (720 mg, 11.5 mmol). After heating at 60° C. for 15 hours, the mixture was cooled and treated with concentrated hydrochloric acid until pH=1. The organics were removed under reduced pressure and the resulting precipitate was collected by filtration, dissolved in ethyl acetate and methanol, and washed with saturated aqueous sodium carbonate. The phases were separated and the organic phase was concentrated to yield 6-chloro-2,3,4,9-tetrahydro-1H-carbazol-1-amine (260 mg, 52% yield) as a light brown solid. $^1$H-NMR (DMSO-$d_6$): δ 10.90 (s, 1H), 7.34 (m, 1H), 7.27 (d, 1H), 6.97 (dd, 1H), 3.90 (t, 1H), 2.54 (m, 2H), 2.04-1.89 (m, 2H), 1.66 (m, 1H), 1.50 (m, 1H); MS m/z 221 (M+1).

Example 3

6-Bromo-2,3,4,9-tetrahydro-1H-carbazol-1-one

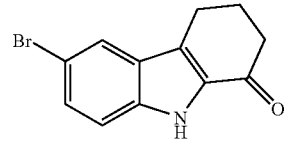

6-Bromo-2,3,4,9-tetrahydro-1H-carbazol-1-one was prepared from bromoaniline and 2-(hydroxymethylene)cyclohexanone in a similar manner as described in Example 1 to give a brown solid. $^1$H-NMR (CDCl$_3$): δ 8.79 (s, 1H), 7.80 (s, 1H), 7.44 (d, 1H), 7.30, (d, 1H), 2.97 (t, 2H), 2.66 (t, 2H), 2.27 (quint, 2H); MS m/z 265 (M+1).

Example 4

6-Bromo-2,3,4,9-tetrahydro-1H-carbazol-1-amine

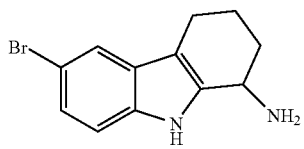

6-Bromo-2,3,4,9-tetrahydro-1H-carbazol-1-amine was prepared in a similar manner as described in Example 2 to give a solid. $^1$H-NMR (CDCl$_3$): δ 8.58 (s, 1H), 7.55 (s, 1H), 7.20 (m, 2H), 4.12 (t, 1H), 2.70 (t, 2H), 2.24 (m, 1H), 2.05 (m, 1H), 1.92 (m, 3H), 1.66 (m, 1H); MS m/z 266 (M+1).

Example 5

6-Methyl-2,3,4,9-tetrahydro-1H-carbazol-1-one

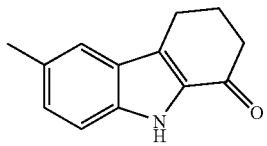

6-Methyl-2,3,4,9-tetrahydro-1H-carbazol-1-one was prepared from p-toluidine and 2-(hydroxymethylene)cyclohexanone in a similar manner as described in Example 1 to give a tan solid. $^1$H-NMR (CDCl$_3$): δ 8.65 (s, 1H), 7.43 (s, 1H), 7.30 (d, 1H), 7.20 (d, 1H), 2.98 (t, 2H), 2.65 (t, 2H), 2.45 (s, 3H), 2.26 (quint, 2H); MS m/z 220 (M+1).

Example 6

6-Methyl-2,3,4,9-tetrahydro-1H-carbazol-1-amine

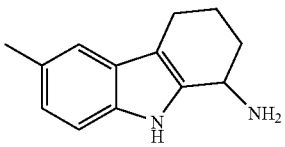

6-Methyl-2,3,4,9-tetrahydro-1H-carbazol-1-amine was prepared in a similar manner as described herein to give a solid. $^1$H-NMR (DMSO-d$_6$): δ 10.5 (s, 1H), 7.15 (d, 1H), 7.11 (s, 1H), 6.81 (d, 1H), 3.98 (t, 1H), 3.30 (s, 2H), 2.53 (t, 2H), 2.32 (s, 3H), 2.02 (m, 1H), 1.90 (m, 1H), 1.68 (m, 1H), 1.65 (m, 1H); MS m/z 201 (M+1).

Example 7

2,3,4,9-Tetrahydro-1H-carbazol-1-one

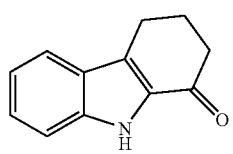

2,3,4,9-Tetrahydro-1H-carbazol-1-one was prepared from aniline and 2-(hydroxymethylene)cyclohexanone in a similar manner as described in Example 1 to give a brown solid. $^1$H-NMR (DMSO-d$_6$): δ 11.6 (s, 1H), 7.66 (d, 1H), 7.38 (d, 1H), 7.30 (t, 1H), 7.07 (t, 1H), 2.90 (t, 2H), 2.56 (t, 2H), 2.15 (quint, 2H); MS m/z 186 (M+1).

Example 8

2,3,4,9-tetrahydro-1H-carbazol-1-amine hydrochloride

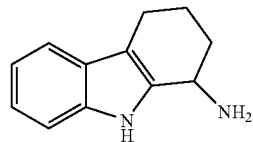

To a solution of 2,3,4,9-tetrahydro-1H-carbazol-1-one (1.5 g, 8.10 mmol) in ethanol (20 mL) was added a solution of hydroxylamine hydrochloride (1.13 g, 16.2 mmol) in water (10 mL) and a solution of sodium acetate (2.19 g, 26.7 mmol) in water (10 mL). The reaction mixture was heated at reflux for 2 h, cooled, and concentrated. The residue was diluted with water and extracted with ethyl acetate (2×100 mL). The organic phase was dried over sodium sulfate, filtered, and concentrated to a brown solid. The oxime was dissolved in THF (80 mL) and lithium aluminum hydride (1.0 M in THF, 24.3 mL) was added dropwise. The reaction was heated at reflux for 7 h and cooled in an ice bath. Methanol was added dropwise until bubbling ceased. The mixture was diluted with aqueous Na/K tartrate, stirred vigorously for 15 min and extracted with ethyl acetate (2×100 mL). The extracts were combined, dried over sodium sulfate, filtered and concentrated. The crude amine was purified by flash chromatography on silica (2% to 5% methanol/methylene chloride gradient) to provide 2,3,4,9-tetrahydro-1H-carbazol-1-amine as a brown oil. The oil was diluted in diethyl ether and HCl (1.0 M in diethyl ether) was added. The resulting precipitate was collected by filtration to provide 2,3,4,9-tetrahydro-1H-carbazol-1-amine hydrochloride (760 mg, 42%) as a light brown solid. $^1$H-NMR (CD$_3$OD): δ 7.54 (d, 1H), 7.42 (d, 1H), 7.22 (t, 1H), 7.09 (t, 1H), 4.66 (t, 1H), 2.95-2.73 (m, 2H), 2.39-2.28 (m, 1H), 2.18-2.03 (m, 3H); MS m/z (M+1) 170.

Example 9

N-(6-Bromo-2,3,4,9-tetrahydro-1H-carbazol-1-yl)-N'-phenylurea

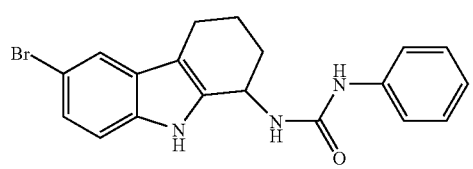

To a solution of 6-bromo-2,3,4,9-tetrahydro-1H-carbazol-1-amine (50 mg, 0.19 mmol) in dichloromethane (1 mL) was added phenyl isocyanate (23 µL, 0.21 mmol). The mixture was stirred at room temperature 15 hours and the resulting precipitate collected by filtration to give a gray solid (62% yield). $^1$H-NMR (DMSO-d$_6$): δ 11.01 (s, 1H), 7.60 (d, 1H), 7.45 (m, 2H), 7.33-7.23 (m, 4H), 7.17 (dd, 1H), 6.94 (m, 1H), 6.63 (d, 1H), 5.02 (m, 1H), 2.68 (m, 2H), 2.06 (m, 1H), 1.95-1.70 (m, 3H); MS m/z 384 (M−1).

Example 10

N-(6-Bromo-2,3,4,9-tetrahydro-1H-carbazol-1-yl)-N'-(4-methoxyphenyl)urea

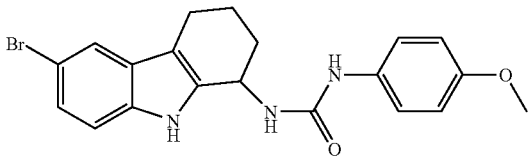

N-(6-Bromo-2,3,4,9-tetrahydro-1H-carbazol-1-yl)-N'-(4-methoxyphenyl)urea was prepared from 6-bromo-2,3,4,9-tetrahydro-1H-carbazol-1-amine and 4-methoxyphenyl isocyanate in a similar manner as described above to give a gray solid (61% yield). $^1$H-NMR (DMSO-d$_6$): δ 10.99 (s, 1H), 8.16 (s, 1H), 7.60 (d, $_1$H), 7.38-7.27 (m, 3H), 7.17 (dd, 1H), 6.87 (d, 2H), 6.52 (d, 1H), 5.01 (m, 1H), 3.73 (s, 3H), 2.67 (m, 2H), 2.04 (m, 1H), 1.94-1.76 (m, 3H); MS m/z 414 (M−1).

Example 11

N-(6-Bromo-2,3,4,9-tetrahydro-1H-carbazol-1-yl)-N'-(4-methoxy-2-methylphenyl)urea

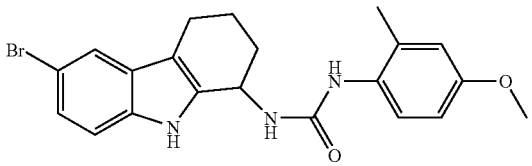

N-(6-Bromo-2,3,4,9-tetrahydro-1H-carbazol-1-yl)-N'-(4-methoxy-2-methylphenyl)urea was prepared from 6-bromo-2,3,4,9-tetrahydro-1H-carbazol-1-amine and 4-methoxy-2-methyl isocyanate in a similar manner as described above to give a dark brown solid (59% yield). $^1$H-NMR (DMSO-d$_6$): δ 11.00 (s, 1H), 7.71 (d, 1H), 7.60 (d, 1H), 7.47 (s, 1H), 7.32 (d, 1H), 7.17 (dd, 1H), 6.88 (d, 1H), 6.75 (m, 2H), 5.00 (m, 1H), 3.73 (s, 3H), 2.69 (m, 2H), 2.18 (s, 3H), 2.04 (m, 1H), 1.94-1.77 (m, 3H); MS m/z 430 (M+1).

Example 12

N-(6-Bromo-2,3,4,9-tetrahydro-1H-carbazol-1-yl)-N'-(3-chloro-4-methoxyphenyl)urea

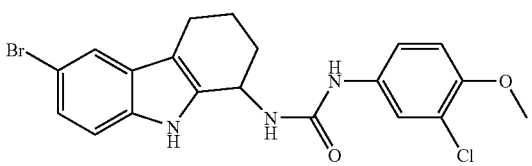

N-(6-Bromo-2,3,4,9-tetrahydro-1H-carbazol-1-yl)-N'-(3-chloro-4-methoxyphenyl)urea was prepared from 6-bromo-2,3,4,9-tetrahydro-1H-carbazol-1-amine and 3-chloro-4-methoxyphenyl isocyanate in a similar manner as described above to give a tan solid (42% yield). $^1$H-NMR (DMSO-d$_6$): δ 10.98 (s, 1H), 8.33 (s, 1H), 7.73 (d, 1H), 7.60 (d, 1H), 7.30 (d, 1H), 7.25-7.14 (m, 2H), 7.08 (d, 1H), 6.63 (d, 1H), 5.01 (m, 1H), 3.82 (s, 3H), 2.65 (m, 2H), 2.04 (m, 1H), 1.94-1.76 (m, 3H); MS m/z 448 (M−1).

Example 13

N-(6-Bromo-2,3,4,9-tetrahydro-1H-carbazol-1-yl)-N'-[4-(dimethylamino)phenyl]urea

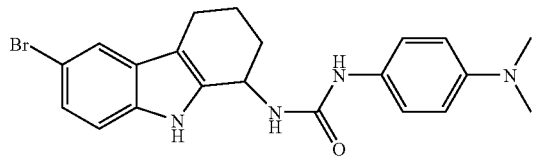

N-(6-Bromo-2,3,4,9-tetrahydro-1H-carbazol-1-yl)-N'-[4-(dimethylamino)phenyl]urea was prepared from 6-bromo-2,3,4,9-tetrahydro-1H-carbazol-1-amine and 4-dimethylamino phenyl isocyanate in a similar manner as described above to give a tan solid (40% yield). $^1$H-NMR (DMSO-d$_6$): δ 10.99 (s, 1H), 7.98 (s, 1H), 7.60 (d, 1H), 7.33-7.23 (m, 3H), 7.17 (dd, 1H), 6.71 (d, 2H), 6.44 (d, 1H), 5.00 (m, 1H), 2.84 (s, 6H), 2.67 (m, 2H), 2.04 (m, 1H), 1.94-1.74 (m, 3H); MS m/z 427 (M−1).

Example 14A

N-(6-Bromo-2,3,4,9-tetrahydro-1H-carbazol-1-yl) benzamide

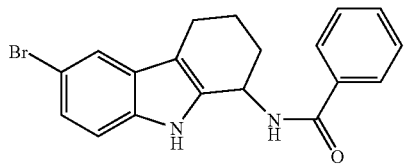

To a solution of 6-bromo-2,3,4,9-tetrahydro-1H-carbazol-1-amine (50 mg, 0.19 mmol) and benzoyl chloride (24 μL, 0.21 mmol) in dichloromethane (1 mL) at 0° C. was added diisopropylethylamine (66 μL, 0.38 mmol). The mixture was stirred at room temperature 15 hours, the solvent removed, and the residue purified by flash chromatography (0-30% ethyl acetate-hexanes) to give 18 mg (26% yield) of a yellow solid. $^1$H-NMR (CDCl$_3$): δ 8.97 (s, 1H), 7.78 (d, 2H), 7.61 (m, 1H), 7.52 (m, 1H), 7.44 (t, 2H), 7.23 (m, 1H), 7.17 (d, 1H), 6.42 (d, 1H), 5.34 (m, 1H), 2.72 (m, 2H), 2.32 (m, 1H), 2.02-1.93 (m, 3H); MS m/z 369 (M−1).

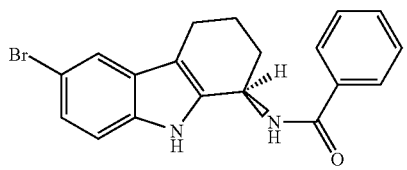

Example 14B

N-[(1R)-6-bromo-2,3,4,9-tetrahydro-1H-carbazol-1-yl]benzamide

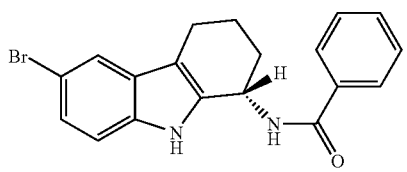

Example 14C

N-[(1S)-6-bromo-2,3,4,9-tetrahydro-1H-carbazol-1-yl]benzamide

N-(6-Bromo-2,3,4,9-tetrahydro-1H-carbazol-1-yl)benzamide was separated on a Berger analytical SFC with an HP1100 diode array detector. The sample was monitored at 230 nm under the following conditions: 30% MeOH in $CO_2$ with a total flow rate of 2 mL/minute at 2250 psi, 50° C. on a Diacel AD-H column (Chiral Technologies), 4.6×250 mm, 5 μm to give N-[(1R)-6-bromo-2,3,4,9-tetrahydro-1H-carbazol-1-yl]benzamide (Example 14B; retention time=12.37 minutes) and N-[(1S)-6-bromo-2,3,4,9-tetrahydro-1H-carbazol-1-yl]benzamide (Example 14C; retention time=16.11 minutes). Chirality assigned by VCD spectroscopy.

Example 15

N-(6-Bromo-2,3,4,9-tetrahydro-1H-carbazol-1-yl)-2-phenylacetamide

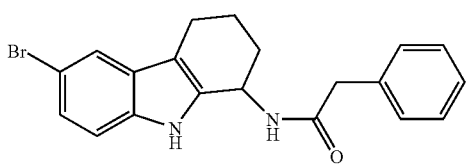

N-(6-Bromo-2,3,4,9-tetrahydro-1H-carbazol-1-yl)-2-phenylacetamide was prepared from 6-bromo-2,3,4,9-tetrahydro-1H-carbazol-1-amine and phenyl acetyl chloride in a similar manner as described above to give a white solid (86% yield). $^1$H-NMR (CDCl$_3$): δ 8.88 (s, 1H), 7.57 (m, 1H), 7.37-7.27 (m, 3H), 7.27-7.20 (m, 3H), 7.15 (d, 1H), 5.74 (d, 1H), 5.08 (m, 1H), 3.61 (s, 2H), 2.62 (m, 2H), 2.13 (m, 1H), 1.81 (m, 2H), 1.67 (m, 1H); MS m/z 383 (M−1).

Example 16

N-(6-Bromo-2,3,4,9-tetrahydro-1H-carbazol-1-yl)-3-phenylpropanamide

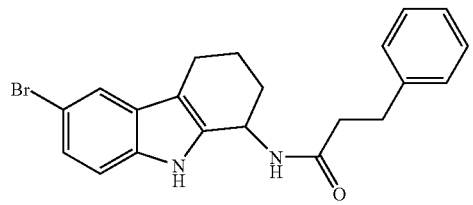

N-(6-Bromo-2,3,4,9-tetrahydro-1H-carbazol-1-yl)-3-phenylpropanamide was prepared from 6-bromo-2,3,4,9-tetrahydro-1H-carbazol-1-amine and hydrocinnamoyl chloride in a similar manner as described above to give a white solid (53% yield). $^1$H-NMR (CDCl$_3$): δ 8.43 (s, 1H), 7.58 (m, 1H), 7.28-7.21 (m, 5H), 7.20-7.15 (m, 2H), 5.51 (d, 1H), 5.05 (m, 1H), 3.00 (t, 2H), 2.62 (m, 2H), 2.58-2.43 (m, 2H), 2.12 (m, 1H), 1.80 (m, 2H), 1.67 (m, 1H); MS m/z 397 (M−1).

Example 17

N-(6-Bromo-2,3,4,9-tetrahydro-1H-carbazol-1-yl)-3-phenylprop-2-enamide

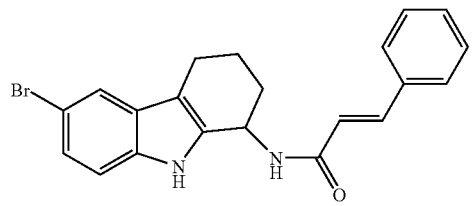

N-(6-Bromo-2,3,4,9-tetrahydro-1H-carbazol-1-yl)-3-phenylprop-2-enamide was prepared from 6-bromo-2,3,4,9-tetrahydro-1H-carbazol-1-amine and cinnamoyl chloride in a similar manner as described above to give an off-white solid (35% yield).
$^1$H-NMR (CDCl$_3$): δ 8.98 (s, 1H), 7.69 (d, 1H), 7.60 (m, 1H), 7.48 (m, 2H), 7.36 (m, 3H), 7.22 (dd, 1H), 7.17 (d, 1H), 6.41 (d, 1H), 5.98 (d, 1H), 5.25 (m, 1H), 2.68 (m, 2H), 2.26 (m, 1H), 1.99-1.84 (m, 3H); MS m/z 395 (M−1).

Example 18

Benzyl 6-bromo-2,3,4,9-tetrahydro-1H-carbazol-1-ylcarbamate

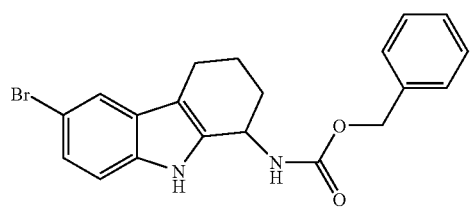

Benzyl 6-bromo-2,3,4,9-tetrahydro-1H-carbazol-1-ylcarbamate was prepared from 6-bromo-2,3,4,9-tetrahydro-1H-carbazol-1-amine and benzyl chloroformate in a similar manner as described above to give a white solid (16% yield). $^1$H-NMR (CDCl$_3$): δ 8.69 (s, 1H), 7.60 (s, 1H), 7.43-7.31 (m, 5H), 7.27-7.21 (m, 1H), 7.17 (d, 1H), 5.16 (q, 2H), 5.08 (m, 1H), 4.92 (m, 1H), 2.66 (m, 2H), 2.20 (m, 1H), 1.89 (m, 2H), 1.80 (m, 1H); MS m/z 400 (M+1).

Example 19

N-(6-Bromo-2,3,4,9-tetrahydro-1H-carbazol-1-yl)-2,6-dichlorobenzamide

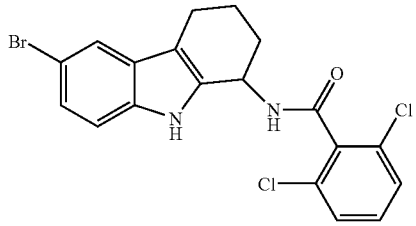

N-(6-Bromo-2,3,4,9-tetrahydro-1H-carbazol-1-yl)-2,6-dichlorobenzamide was prepared from 6-bromo-2,3,4,9-tetrahydro-1H-carbazol-1-amine and 2,6-dichlorobenzoyl chloride in a similar manner as described above to give a white solid (25% yield). $^1$H-NMR (DMSO-d$_6$): δ 10.80 (s, 1H), 9.18 (d, 1H), 7.61 (d, 1H), 7.52 (d, 1H), 7.49 (d, 1H), 7.43 (dd, 1H), 7.36 (d, 1H), 7.19 (dd, 1H), 5.27 (m, 1H), 2.69 (m, 2H), 2.08-1.82 (m, 4H); MS m/z 437 (M−1).

Example 20

N-(6-Bromo-2,3,4,9-tetrahydro-1H-carbazol-1-yl)-4-fluorobenzamide

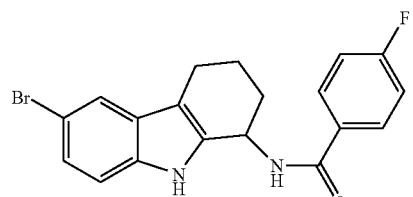

N-(6-Bromo-2,3,4,9-tetrahydro-1H-carbazol-1-yl)-4-fluorobenzamide was prepared from 6-bromo-2,3,4,9-tetrahydro-1H-carbazol-1-amine and 4-fluorobenzoyl chloride in a similar manner as described above to give a white solid (15% yield). $^1$H-NMR (DMSO-d$_6$): δ 11.03 (s, 1H), 8.90 (d, 1H), 8.05 (m, 2H), 7.61 (d, 1H), 7.34 (d, 2H), 7.30 (s, 1H), 7.17 (dd, 1H), 5.38 (m, 1H), 2.68 (m, 2H), 2.09 (m, 2H), 1.86 (m, 2H); MS m/z 387 (M−1).

Example 21

N-(6-Bromo-2,3,4,9-tetrahydro-1H-carbazol-1-yl)-4-methoxybenzamide

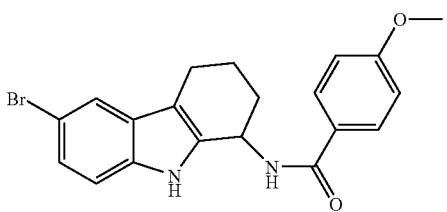

N-(6-Bromo-2,3,4,9-tetrahydro-1H-carbazol-1-yl)-4-methoxybenzamide was prepared from 6-bromo-2,3,4,9-tetrahydro-1H-carbazol-1-amine and p-anisoyl chloride in a similar manner as described above to give a white solid (11% yield). $^1$H-NMR (DMSO-de): δ10.99 (s, 1H), 8.70 (d, 1H), 7.96 (d, 2H), 7.60 (d, 1H), 7.29 (d, 1H), 7.16 (dd, 1H), 7.02 (d, 2H), 5.38 (m, 1H), 2.67 (m, 2H), 2.08 (m, 2H), 1.87 (m, 2H); MS m/z 399 (M−1).

Example 22

N-(6-Bromo-2,3,4,9-tetrahydro-1H-carbazol-1-yl)-4-nitrobenzamide

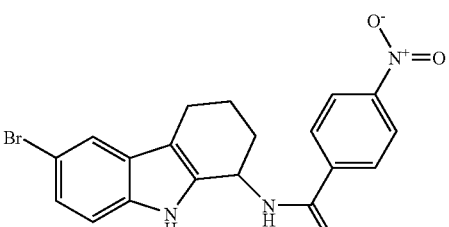

N-(6-Bromo-2,3,4,9-tetrahydro-1H-carbazol-1-yl)-4-nitrobenzamide was prepared from 6-bromo-2,3,4,9-tetrahydro-1H-carbazol-1-amine and 4-nitrobenzoyl chloride in a similar manner as described above to give an orange solid (32% yield). $^1$H-NMR (DMSO-d$_6$): δ 11.11 (s, 1H), 9.24 (d, 1H), 8.36 (d, 2H), 8.19 (d, 2H), 7.62 (m, 1H), 7.29 (d, 1H), 7.18 (dd, 1H), 5.41 (m, 1H), 2.69 (m, 2H), 2.10 (m, 2H), 1.89 (m, 2H); MS m/z 414 (M−1).

Example 23

N-(6-Bromo-2,3,4,9-tetrahydro-1H-carbazol-1-yl)-4-chlorobenzamide

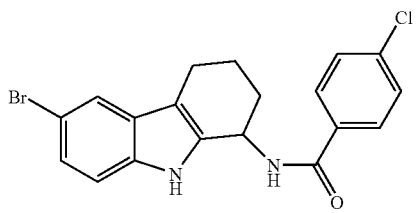

N-(6-Bromo-2,3,4,9-tetrahydro-1H-carbazol-1-yl)-4-chlorobenzamide was prepared from 6-bromo-2,3,4,9-tetrahydro-1H-carbazol-1-amine and 4-chlorobenzoyl chloride in a similar manner as described above to give a tan solid (69% yield). $^1$H-NMR (CDCl$_3$): δ 8.89 (s, 1H), 7.71 (d, 2H), 7.60 (m, 1H), 7.40 (d, 2H), 7.23 (dd, 1H), 7.17 (dd, 1H), 6.36 (d, 1H), 5.30 (m, 1H), 2.69 (m, 2H), 2.29 (m, 1H), 1.96 (m, 3H); MS m/z 403 (M−1).

Example 24

N-(6-Bromo-2,3,4,9-tetrahydro-1H-carbazol-1-yl)-4-methylbenzamide

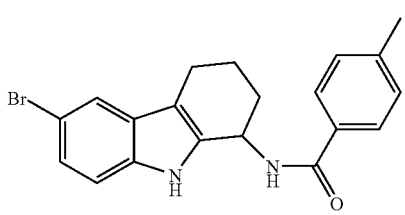

N-(6-Bromo-2,3,4,9-tetrahydro-1H-carbazol-1-yl)-4-methylbenzamide was prepared from 6-bromo-2,3,4,9-tetrahydro-1H-carbazol-1-amine and p-toluyl chloride in a similar manner as described above to give a yellow solid (62% yield). $^1$H-NMR (CDCl$_3$): δ 8.97 (s, 1H), 7.67 (d, 2H), 7.61 (m, 1H), 7.25-7.20 (m, 3H), 7.17 (d, 1H), 6.36 (d, 1H), 5.30 (m, 1H), 2.71 (m, 2H), 2.39 (s, 3H), 2.30 (m, 1H), 1.97 (m, 3H); MS m/z 383 (M−1).

Example 25

N-(6-Bromo-2,3,4,9-tetrahydro-1H-carbazol-1-yl)-4-(trifluoromethyl)benzamide

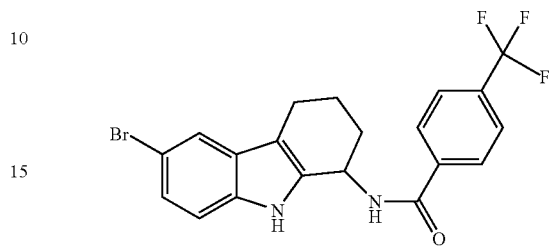

N-(6-Bromo-2,3,4,9-tetrahydro-1H-carbazol-1-yl)-4-(trifluoromethyl)benzamide was prepared from 6-bromo-2,3,4,9-tetrahydro-1H-carbazol-1-amine and 4-trifluoromethyl benzoyl chloride in a similar manner as described above to give a tan solid (63% yield). $^1$H-NMR (CDCl$_3$): δ 8.83 (s, 1H), 7.89 (d, 2H), 7.70 (d, 2H), 7.61 (m, 1H), 7.23 (d, 1H), 7.18 (d, 1H), 6.42 (d, 1H), 5.33 (m, 1H), 2.72 (m, 2H), 2.31 (m, 1H), 1.97 (m, 3H); MS m/z 437 (M−1).

Example 26

N-(6-Bromo-2,3,4,9-tetrahydro-1H-carbazol-1-yl)-3-fluorobenzamide

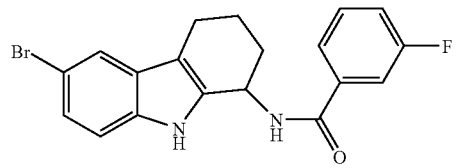

N-(6-Bromo-2,3,4,9-tetrahydro-1H-carbazol-1-yl)-3-fluorobenzamide was prepared from 6-bromo-2,3,4,9-tetrahydro-1H-carbazol-1-amine and 3-fluorobenzoyl chloride in a similar manner as described above to give a white solid (24% yield). $^1$H-NMR (DMSO-d$_6$): δ 11.04 (s, 1H), 8.97 (d, 1H), 7.85-7.81 (m, 1H), 7.81-7.74 (m, 1H), 7.62 (d, 1H), 7.59-7.50 (m, 1H), 7.46-7.37 (m, 1H), 7.29 (d, 1H), 7.17 (dd, 1H), 5.38 (m, 1H), 2.68 (m, 2H), 2.08 (m, 2H), 1.87 (m, 2H); MS m/z 387 (M−1).

Example 27

N-(6-Bromo-2,3,4,9-tetrahydro-1H-carbazol-1-yl)-3-methoxybenzamide

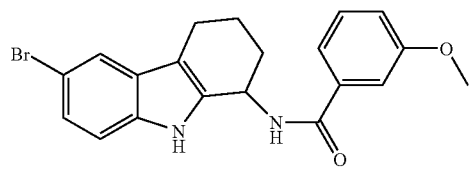

N-(6-Bromo-2,3,4,9-tetrahydro-1H-carbazol-1-yl)-3-methoxybenzamide was prepared from 6-bromo-2,3,4,9-tetrahydro-1H-carbazol-1-amine and m-anisoyl chloride in a similar manner as described above to give an orange solid (49% yield). $^1$H-NMR (CDCl$_3$): δ 8.92 (s, 1H), 7.61 (m, 1H), 7.38-7.30 (m, 2H), 7.30-7.25 (m, 1H), 7.23 (m, 1H), 7.17 (d, 1H), 7.08-7.02 (m, 1H), 6.39 (d, 1H), 5.32 (m, 1H), 3.85 (s, 3H), 2.72 (m, 2H), 2.31 (m, 1H), 1.97 (m, 3H); MS m/z 399 (M−1).

Example 28

N-(6-Bromo-2,3,4,9-tetrahydro-1H-carbazol-1-yl)-3-methylbenzamide

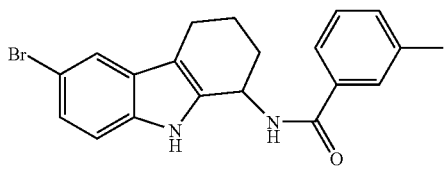

N-(6-Bromo-2,3,4,9-tetrahydro-1H-carbazol-1-yl)-3-methylbenzamide was prepared from 6-bromo-2,3,4,9-tetrahydro-1H-carbazol-1-amine and m-toluoyl chloride in a similar manner as described above to give a tan solid (51% yield). $^1$H-NMR (CDCl$_3$): δ 8.95 (s, 1H), 7.63-7.59 (m, 2H), 7.55 (m, 1H), 7.33 (m, 2H), 7.23 (m, 1H), 7.17 (d, 1H), 6.38 (d, 1H), 5.32 (m, 1H), 2.72 (m, 2H), 2.40 (s, 3H), 2.31 (m, 1H), 1.98 (m, 3H); MS m/z 383 (M−1).

Example 29

N-(6-Bromo-2,3,4,9-tetrahydro-1H-carbazol-1-yl)-2-fluorobenzamide

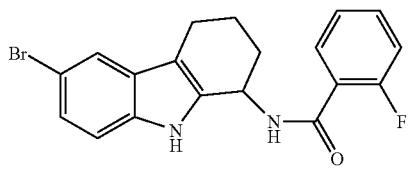

N-(6-Bromo-2,3,4,9-tetrahydro-1H-carbazol-1-yl)-2-fluorobenzamide was prepared from 6-bromo-2,3,4,9-tetrahydro-1H-carbazol-1-amine and 2-fluorobenzoyl chloride in a similar manner as described above to give a yellow solid (57% yield). $^1$H-NMR (CDCl$_3$): δ 8.91 (s, 1H), 8.15 (m, 1H), 7.62 (m, 1H), 7.50 (m, 1H), 7.30 (m, 1H), 7.23 (dd, 1H), 7.18 (d, 1H), 7.12 (m, 2H), 5.35 (m, 1H), 2.72 (m, 2H), 2.31 (m, 1H), 1.98 (m, 3H); MS m/z 387 (M−1).

Example 30

N-(6-Bromo-2,3,4,9-tetrahydro-1H-carbazol-1-yl)-2-methoxybenzamide

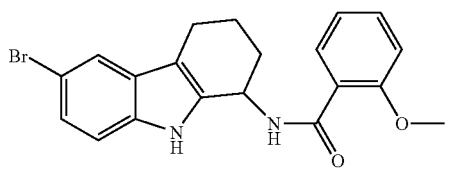

N-(6-Bromo-2,3,4,9-tetrahydro-1H-carbazol-1-yl)-2-methoxybenzamide was prepared from 6-bromo-2,3,4,9-tetrahydro-1H-carbazol-1-amine and o-anisoyl chloride in a similar manner as described above to give a pale orange solid (67% yield). $^1$H-NMR (CDCl$_3$): δ 9.06 (s, 1H), 8.31 (d, 1H), 8.25 (dd, 1H), 7.60 (d, 1H), 7.46 (m, 1H), 7.20 (dd, 1H), 7.17 (dd, 1H), 7.10 (m, 1H), 6.96 (d, 1H), 5.31 (m, 1H), 3.91 (s, 3H), 2.72 (m, 2H), 2.31 (m, 1H), 1.98 (m, 3H); MS m/z 399 (M−1).

Example 31

N-(6-Bromo-2,3,4,9-tetrahydro-1H-carbazol-1-yl)-2-nitrobenzamide

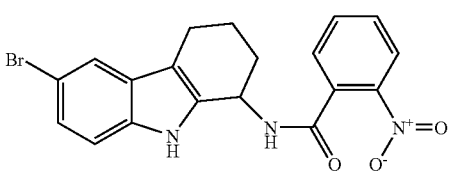

N-(6-Bromo-2,3,4,9-tetrahydro-1H-carbazol-1-yl)-2-nitrobenzamide was prepared from 6-bromo-2,3,4,9-tetrahydro-1H-carbazol-1-amine and 2-nitrobenzoyl chloride in a similar manner as described above to give an orange solid (39% yield). $^1$H-NMR (CDCl$_3$): δ 8.73 (s, 1H), 8.08 (m, 1H), 7.68 (m, 1H), 7.60 (m, 2H), 7.54 (m, 1H), 7.29-7.21 (m, 2H), 6.15 (d, 1H), 5.42 (m, 1H), 2.69 (m, 2H), 2.33 (m, 1H), 1.96 (m, 3H); MS m/z 414 (M−1).

Example 32

N-(6-Bromo-2,3,4,9-tetrahydro-1H-carbazol-1-yl)-2-chlorobenzamide

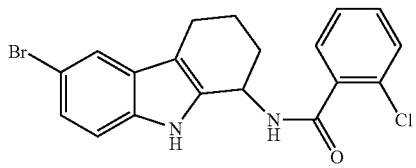

N-(6-Bromo-2,3,4,9-tetrahydro-1H-carbazol-1-yl)-2-chlorobenzamide was prepared from 6-bromo-2,3,4,9-tetrahydro-1H-carbazol-1-amine and 2-chlorobenzoyl chloride in a similar manner as described above to give a white solid (30% yield). $^1$H-NMR (DMSO-$d_6$): δ 10.98 (s, 1H), 8.89 (d, 1H), 7.54 (dd, 2H), 7.48-7.44 (m, 1H), 7.42 (dd, 1H), 7.40-7.34 (m, 1H), 7.28 (d, 1H), 7.13 (dd, 1H), 5.26 (m, 1H), 2.60 (m, 2H), 2.08-1.91 (m, 2H), 1.90-1.73 (m, 2H); MS m/z 403 (M−1).

Example 33

N-(6-Bromo-2,3,4,9-tetrahydro-1H-carbazol-1-yl)-2-methylbenzamide

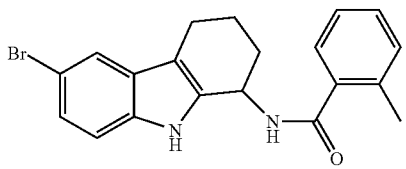

N-(6-Bromo-2,3,4,9-tetrahydro-1H-carbazol-1-yl)-2-methylbenzamide was prepared from 6-bromo-2,3,4,9-tetrahydro-1H-carbazol-1-amine and o-toluoyl chloride in a similar manner as described above to give a gray solid (19% yield). $^1$H-NMR (DMSO-$d_6$): δ 11.01 (s, 1H), 8.70 (d, 1H), 7.59 (m, 1H), 7.47 (d, 1H), 7.33 (m, 2H), 7.26 (m, 2H), 7.17 (dd, 1H), 5.34 (m, 1H), 2.65 (m, 2H), 2.42 (s, 3H), 2.07 (m, 2H), 1.87 (m, 2H); MS m/z 383 (M−1).

Example 34

N-(2,3,4,9-Tetrahydro-1H-carbazol-1-yl)benzamide

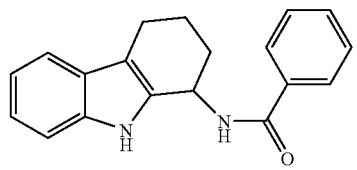

N-(2,3,4,9-Tetrahydro-1H-carbazol-1-yl)benzamide was prepared from 2,3,4,9-tetrahydro-1H-carbazol-1-amine hydrochloride and benzoyl chloride in a similar manner as described above to give a pale yellow solid (73% yield). $^1$H-NMR (CDCl$_3$): δ 8.79 (s, 1H), 7.81-7.75 (m, 2H), 7.54-7.48 (m, 2H), 7.47-7.40 (m, 2H), 7.32 (d, 1H), 7.17 (m, 1H), 7.09 (d, 1H), 6.42 (d, 1H), 5.37 (m, 1H), 2.78 (m, 2H), 2.32 (m, 1H), 2.03-1.91 (m, 3H); MS m/z 289 (M−1).

Example 35

N-(6-Methyl-2,3,4,9-tetrahydro-1H-carbazol-1-yl)benzamide

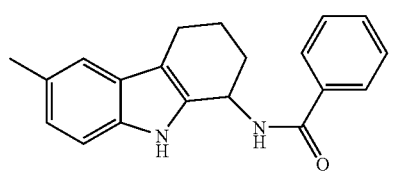

N-(6-Methyl-2,3,4,9-tetrahydro-1H-carbazol-1-yl)benzamide was prepared from 6-methyl-2,3,4,9-tetrahydro-1H-carbazol-1-amine and benzoyl chloride in a similar manner as described above to give a pale yellow solid (81% yield). $^1$H-NMR (CDCl$_3$): δ 8.63 (s, 1H), 7.81-7.75 (m, 2H), 7.54-7.48 (m, 1H), 7.47-7.40 (m, 2H), 7.28 (m, 1H), 7.20 (d, 1H), 6.99 (dd, 1H), 6.40 (d, 1H), 5.36 (m, 1H), 2.75 (m, 2H), 2.44 (s, 3H), 2.31 (m, 1H), 2.02-1.91 (m, 3H); MS m/z 303 (M−1).

Example 36A

N-(6-Chloro-2,3,4,9-tetrahydro-1H-carbazol-1-yl)benzamide

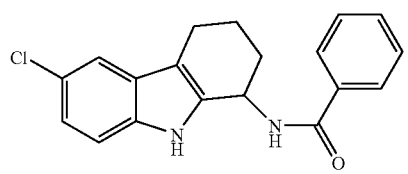

N-(6-Chloro-2,3,4,9-tetrahydro-1H-carbazol-1-yl)benzamide was prepared from 6-chloro-2,3,4,9-tetrahydro-1H-carbazol-1-amine and benzoyl chloride in a similar manner as described above to give a pale yellow solid (81% yield). $^1$H-NMR (CDCl$_3$): δ 9.02 (s, 1H), 7.79-7.73 (m, 2H), 7.54-7.48 (m, 1H), 7.46-7.39 (m, 3H), 7.21 (d, 1H), 7.10 (dd, 1H), 6.45 (d, 1H), 5.32 (m, 1H), 2.72 (m, 2H), 2.30 (m, 1H), 2.01-1.90 (m, 3H); MS m/z 323 (M−1).

Example 36B

N-[(1R)-6-chloro-2,3,4,9-tetrahydro-1H-carbazol-1-yl]benzamide

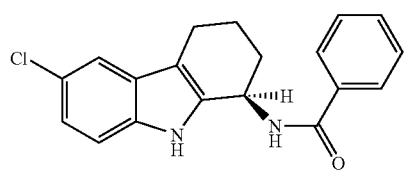

Example 36C

N-[(1S)-6-chloro-2,3,4,9-tetrahydro-1H-carbazol-1-yl]benzamide

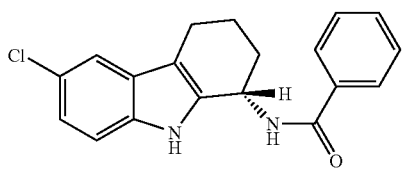

N-(6-Chloro-2,3,4,9-tetrahydro-1H-carbazol-1-yl)benzamide was separated on a Berger analytical SFC with an HP1100 diode array detector. The sample was monitored at 230 nm under the following conditions: 30% MeOH in $CO_2$ with a total flow rate of 2 mL/minute at 1500 psi, 40° C. on a Diacel AS-H column (Chiral Technologies), 4.6×250 mm, 5 µm to give R-N-(6-chloro-2,3,4,9-tetrahydro-1H-carbazol-1-yl)benzamide (retention time=5.08 minutes) and S-N-(6-chloro-2,3,4,9-tetrahydro-1H-carbazol-1-yl)benzamide (retention time=7.45 minutes). Chirality assigned by VCD spectroscopy.

Example 37

N-(6-Bromo-2,3,4,9-tetrahydro-1H-carbazol-1-yl)-4-methylbenzenesulfonamide

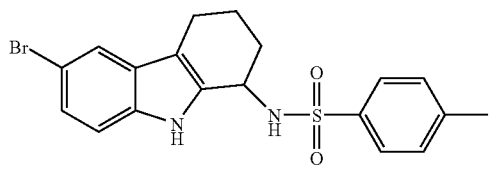

N-(6-Bromo-2,3,4,9-tetrahydro-1H-carbazol-1-yl)4-methylbenzenesulfonamide was prepared from 6-bromo-2,3,4,9-tetrahydro-1H-carbazol-1-amine and p-toluene sulfonyl chloride in a similar manner as described above to give a tan solid (60% yield). $^1$H-NMR (CDCl$_3$): δ 8.63 (s, 1H), 7.85 (d, 2H), 7.57 (m, 1H), 7.37 (d, 2H), 7.25 (m, 1H), 7.18 (d, 1H), 4.74 (d, 1H), 4.46 (m, 1H), 2.61 (m, 2H), 2.48 (s, 3H), 2.00-1.82 (m, 2H), 1.80-1.60 (m, 2H); MS m/z 419 (M−1).

Example 38

N-(6-Bromo-2,3,4,9-tetrahydro-1H-carbazol-1-yl)pyridine-2-carboxamide

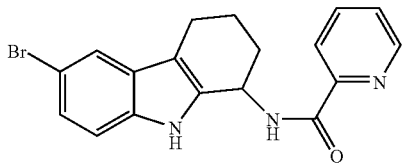

N-(6-Bromo-2,3,4,9-tetrahydro-1H-carbazol-1-yl)pyridine-2-carboxamide was prepared from 6-bromo-2,3,4,9-tetrahydro-1H-carbazol-1-amine and picolinoyl chloride in a similar manner as described above to give an off-white solid (64% yield). $^1$H-NMR (CDCl$_3$): δ 8.96 (s, 1H), 8.52 (m, 1H), 8.37 (d, 1H), 8.21 (m, 1H), 7.86 (m, 1H), 7.61 (m, 1H), 7.43 (m, 1H), 7.22 (dd, 1H), 7.17 (d, 1H), 5.31 (m, 1H), 2.72 (m, 2H), 2.31 (m, 1H), 1.98 (m, 3H); MS m/z 370 (M−1).

Example 39

N-(6-Bromo-2,3,4,9-tetrahydro-1H-carbazol-1-yl)nicotinamide

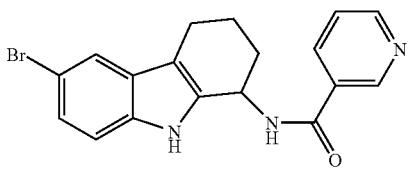

N-(6-Bromo-2,3,4,9-tetrahydro-1H-carbazol-1-yl)nicotinamide was prepared from 6-bromo-2,3,4,9-tetrahydro-1H-carbazol-1-amine and nicotinyl chloride in a similar manner as described above to give a white solid (54% yield). $^1$H-NMR (DMSO-d$_6$): δ 11.02 (s, 1H), 9.08-9.00 (m, 2H), 8.69 (dd, 1H), 8.25 (m, 1H), 7.57 (d, 1H), 7.53-7.43 (m, 1H), 7.24 (d, 1H), 7.13 (dd, 1H), 5.35 (m, 1H), 2.64 (m, 2H), 2.04 (m, 2H), 1.84 (m, 2H); MS m/z 370 (M−1).

Example 40

N-(6-Bromo-2,3,4,9-tetrahydro-1H-carbazol-1-yl)-6-chloronicotinamide

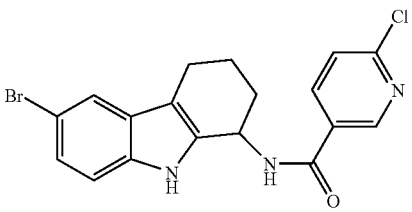

N-(6-Bromo-2,3,4,9-tetrahydro-1H-carbazol-1-yl)-6-chloronicotinamide was prepared from 6-bromo-2,3,4,9-tetrahydro-1H-carbazol-1-amine and 6-chloronicotinyl chloride in a similar manner as described above to give a white solid (48% yield). $^1$H-NMR (DMSO-d$_6$): δ 11.04 (s, 1H), 9.12 (d, 1H), 8.88 (dd, 1H), 8.30 (dd, 1H), 7.64 (dd, 1H), 7.57 (d, 1H), 7.24 (m, 1H), 7.13 (dd, 1H), 5.34 (m, 1H), 2.63 (m, 2H), 2.04 (m, 2H), 1.82 (m, 2H); MS m/z 404 (M−1).

Example 41

N-(6-Bromo-2,3,4,9-tetrahydro-1H-carbazol-1-yl)isonicotinamide

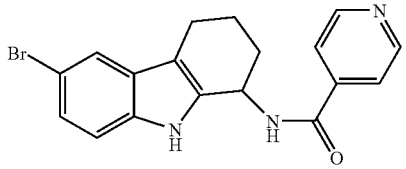

N-(6-Bromo-2,3,4,9-tetrahydro-1H-carbazol-1-yl)isonicotinamide was prepared from 6-bromo-2,3,4,9-tetrahydro-1H-carbazol-1-amine and isonicotinyl chloride in a similar manner as described above to give a white solid (30% yield). $^1$H-NMR (DMSO-$d_6$): δ 11.04 (s, 1H), 9.13 (d, 1H), 8.71 (m, 2H), 7.82 (m, 2H), 7.57 (d, 1H), 7.24 (d, 1H), 7.13 (dd, 1H), 5.35 (m, 1H), 2.64 (m, 2H), 2.04 (m, 2H), 1.84 (m, 2H); MS m/z 370 (M−1).

Example 42

N-Phenyl-N'-(2,3,4,9-tetrahydro-1H-carbazol-1-yl)urea

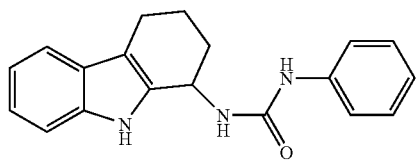

N-Phenyl-N'-(2,3,4,9-tetrahydro-1H-carbazol-1-yl)urea was prepared from 2,3,4,9-tetrahydro-1H-carbazol-1-amine hydrochloride and phenyl isocyanate in a similar manner as described above to give a white solid (60% yield). $^1$H-NMR (DMSO-$d_6$): δ 10.72 (s, 1H), 8.28 (s, 1H), 7.43-7.33 (m, 3H), 7.29-7.17 (m, 3H), 7.00 (m, 1H), 6.94-6.83 (m, 2H), 6.52 (d, 1H), 4.95 (m, 1H), 2.62 (m, 2H), 1.99 (m, 1H), 1.88-1.70 (m, 3H); MS m/z 304 (M−1).

Example 43

N-(6-Methyl-2,3,4,9-tetrahydro-1H-carbazol-1-yl)-N'-phenylurea

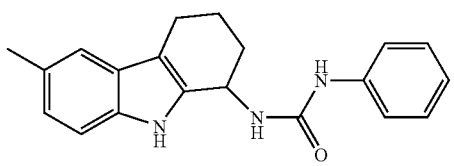

N-(6-Methyl-2,3,4,9-tetrahydro-1H-carbazol-1-yl)-N'-phenylurea was prepared from 6-methyl-2,3,4,9-tetrahydro-1H-carbazol-1-amine and phenyl isocyanate in a similar manner as described above to give a white solid (82% yield). $^1$H-NMR (DMSO-$d_6$): δ 10.57 (s, 1H), 8.27 (s, 1H), 7.42- 7.34 (m, 2H), 7.20 (m, 2H), 7.17-7.11 (m, 2H), 6.87 (m, 1H), 6.82 (m, 1H), 6.51 (d, 1H), 4.92 (m, 1H), 2.58 (m, 2H), 2.32 (s, 3H), 1.97 (m, 1H), 1.87-1.70 (m, 3H); MS m/z 318 (M−1).

Example 44

N-(6-Chloro-2,3,4,9-tetrahydro-1H-carbazol-1-yl)-N'-phenylurea

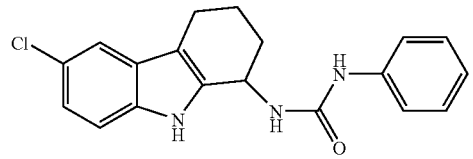

N-(6-Chloro-2,3,4,9-tetrahydro-1H-carbazol-1-yl)-N'-phenylurea was prepared from 6-chloro-2,3,4,9-tetrahydro-1H-carbazol-1-amine and phenyl isocyanate in a similar manner as described above to give a white solid (74% yield). $^1$H-NMR (DMSO-$d_6$): δ 10.93 (s, 1H), 8.30 (s, 1H), 7.41-7.36 (m, 3H), 7.28 (d, 1H), 7.21 (m, 2H), 7.00 (dd, 1H), 6.88 (m, 1H), 6.57 (d, 1H), 4.95 (m, 1H), 2.59 (m, 2H), 1.98 (m, 1H), 1.88-1.70 (m, 3H); MS m/z 338 (M−1).

Example 45A

N-(6-Chloro-2,3,4,9-tetrahydro-1H-carbazol-1-yl)-2-pyridinecarboxamide

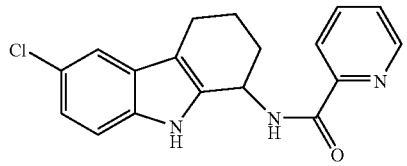

N-(6-Chloro-2,3,4,9-tetrahydro-1H-carbazol-1-yl)-2-pyridinecarboxamide was prepared from 6-chloro-2,3,4,9-tetrahydro-1H-carbazol-1-amine and picolinoyl chloride in a similar manner as described in Example 14 to give an off-white solid (62% yield). $^1$H-NMR (DMSO-$d_6$): δ 10.93 (s, 1H), 8.78 (d, 1H), 8.61 (m, 1H), 8.12 (m, 1H), 8.02 (m, 1H), 7.61 (m, 1H), 7.43 (m, 1H), 7.26 (d, 1H), 7.01 (dd, 1H), 5.34 (m, 1H), 2.64 (m, 2H), 2.00 (m, 3H), 1.82 (m, 1H); MS m/z 348 (M+Na).

Example 45B

N-[(1R)-6-chloro-2,3,4,9-tetrahydro-1H-carbazol-1-yl]pyridine-2-carboxamide

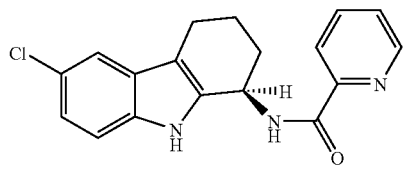

N-(6-Chloro-2,3,4,9-tetrahydro-1H-carbazol-1-yl)-2-pyridinecarboxamide was separated on a Berger analytical SFC with an HP1100 diode array detector. The sample was monitored at 230 nm under the following conditions: 30% MeOH in $CO_2$ with a total flow rate of 2 mL/minute at 1500 psi, 40° C. on a Diacel AS-H column (Chiral Technologies), 4.6×250 mm, 5 μm to give N-[(1R)-6-chloro-2,3,4,9-tetrahydro-1H-carbazol-1-yl]pyridine-2-carboxamide (retention time=4.55 minutes); $[\alpha]_D$=+86; R configuration confirmed by VCD and X-ray crystallography; $^1$H-NMR and MS identical to racemic compound; $^{13}$C-NMR (DMSO-$d_6$): δ 164.1, 150.6, 149.1, 138.4, 136.4, 135.3, 128.5, 127.2, 123.7, 122.7, 121.5, 117.8, 113.4, 111.2, 44.0, 30.8, 21.5, 21.0; HR MS m/z 348.0876 (M+Na); Analytical Calculated for $C_{18}H_{16}ClN_3O$ with ¼$H_2O$: C, 65.45; H, 5.04; N, 12.72. Found: C, 65.67; H, 4.91; N, 12.66. LC-UV purity check: Waters analytical LC-UV consisting of a Waters 626 pumping system, a Waters 996 diode array detector, and a Gilson 233XL autosampler; column: Waters Symmetry Shield RP18, 3.9×150 mm, 5 m; 50-90% acetonitrile-water (0.1% formic acid); total run time of 15 minutes; flow rate remains constant at 1.5 mL/minute; retention time=7.41 minutes.

Example 45C

N-[(1S)-6-chloro-2,3,4,9-tetrahydro-1H-carbazol-1-yl]pyridine-2-carboxamide

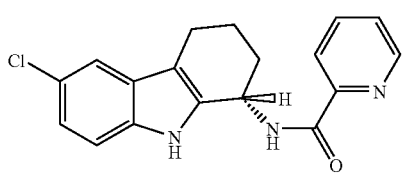

N-(6-Chloro-2,3,4,9-tetrahydro-1H-carbazol-1-yl)-2-pyridinecarboxamide was separated on a Berger analytical SFC with an HP1100 diode array detector. The sample was monitored at 230 nm under the following conditions: 30% MeOH in $CO_2$ with a total flow rate of 2 mL/minute at 1500 psi, 40° C. on a Diacel AS-H column (Chiral Technologies), 4.6×250 mm, 5 μm to give N-[(1S)-6-chloro-2,3,4,9-tetrahydro-1H-carbazol-1-yl]pyridine-2-carboxamide (retention time=6.77 minutes; $[\alpha]_D$=−86); $^1$H-NMR and MS identical to racemic compound. Stereochemistry assigned by VCD.

Example 46A

N-(6-Chloro-2,3,4,9-tetrahydro-1H-carbazol-1-yl)-2-fluorobenzamide

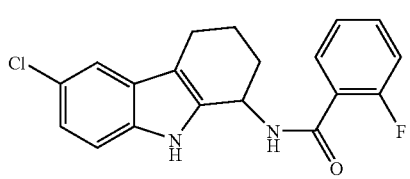

N-(6-Chloro-2,3,4,9-tetrahydro-1H-carbazol-1-yl)-2-fluorobenzamide was prepared from 6-chloro-2,3,4,9-tetrahydro-1H-carbazol-1-amine and 2-fluorobenzoyl chloride in a similar manner as described in Example 14 to give a white solid (63% yield). $^1$H-NMR (CDCl$_3$): δ 8.93 (s, 1H), 8.14 (m, 1H), 7.49 (m, 1H), 7.45 (m, 1H), 7.28 (m, 1H), 7.22 (d, 1H), 7.10 (m, 3H), 5.35 (m, 1H), 2.72 (m, 2H), 2.31 (m, 1H), 1.98 (m, 3H); MS m/z 343 (M+1).

Example 46B

N-[(1R)-6-chloro-2,3,4,9-tetrahydro-1H-carbazol-1-yl]-2-fluorobenzamide

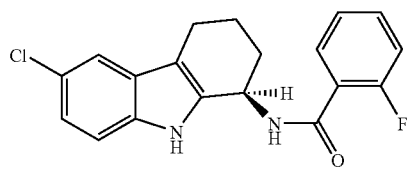

Example 46C

N-[(1S)-6-chloro-2,3,4,9-tetrahydro-1H-carbazol-1-yl]-2-fluorobenzamide

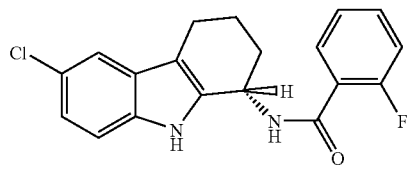

N-(6-Chloro-2,3,4,9-tetrahydro-1H-carbazol-1-yl)-2-fluorobenzamide was separated on a Berger analytical SFC with an HP1100 diode array detector. The sample was monitored at 254 nm under the following conditions: 30% MeOH in $CO_2$ with a total flow rate of 2 mL/minute at 2250 psi, 40° C. on a Diacel OJ-H column (Chiral Technologies), 4.6×250 mm, 5 μm to give N-[(1S)-6-chloro-2,3,4,9-tetrahydro-1H-carbazol-1-yl]-2-fluorobenzamide (retention time=6.29 minutes) and N-[(1R)-6-chloro-2,3,4,9-tetrahydro-1H-carbazol-1-yl]-2-fluorobenzamide (retention time=9.32 minutes).

Example 47

N-(6-Chloro-2,3,4,9-tetrahydro-1H-carbazol-1-yl)-1-methyl-1H-imidazole-5-carboxamide

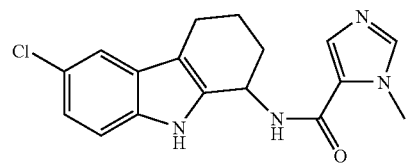

To a solution of 1-methyl-1H-imidazole-5-carboxylic acid (45 mg, 0.36 mmol) in dichloromethane (3.6 mL) was added 6-chloro-2,3,4,9-tetrahydro-1H-carbazol-1-amine (95 mg, 0.43 mmol), 1-ethyl-3-(3-dimethylaminopropyl)carbodiimide (83 mg, 0.43 mmol), and 1-hydroxybenzotriazole (54 mg, 0.40 mmol). After 5 minutes, triethylamine (100 μL, 0.72 mmol) was added and the reaction was stirred at room temperature for 15 hours. The reaction mixture was diluted with dichloromethane, washed with water, 1 N hydrochloric acid, 1 N sodium hydroxide, brine, dried with magnesium sulfate, filtered, and concentrated. The residue was purified by preparative chromatography (10-90% acetonitrile-water (0.1% trifluoroacetic acid)) and then diluted with ethyl acetate, washed with saturated aqueous sodium bicarbonate, and dried with magnesium sulfate to give 43 mg (36% yield) of a white solid. $^1$H-NMR (CDCl$_3$): δ 9.21 (s, 1H), 7.43 (m, 1H), 7.32 (s, 1H), 7.30 (s, 1H), 7.20 (d, 1H), 7.07 (dd, 1H), 6.60 (d, 1H), 5.25 (m, 1H), 3.81 (s, 3H), 2.67 (m, 2H), 2.21 (m, 1H), 1.90 (m, 3H); MS m/z 327 (M−1).

Example 48

N-(6-Chloro-2,3,4,9-tetrahydro-1H-carbazol-1-yl)-1-methyl-1H-pyrazole-5-carboxamide

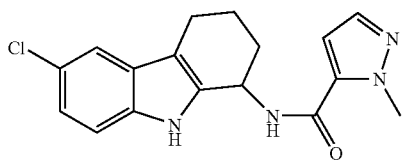

N-(6-Chloro-2,3,4,9-tetrahydro-1H-carbazol-1-yl)-1-methyl-1H-pyrazole-5-carboxamide was prepared from 2-methyl-2H-pyrazole-3-carboxylic acid and 6-chloro-2,3,4,9-tetrahydro-1H-carbazol-1-amine in a similar manner as described above to give a white solid (30% yield). $^1$H-NMR (CDCl$_3$): δ 8.69 (s, 1H), 7.45 (m, 2H), 7.22 (d, 1H), 7.10 (dd, 1H), 6.48 (d, 1H), 6.26 (d, 1H), 5.28 (m, 1H), 4.22 (s, 3H), 2.71 (m, 2H), 2.28 (m, 1H), 1.95 (m, 3H); MS m/z 327 (M−1).

Example 49

N-(6-Chloro-2,3,4,9-tetrahydro-1H-carbazol-1-yl)-1-methyl-1H-pyrazole-3-carboxamide

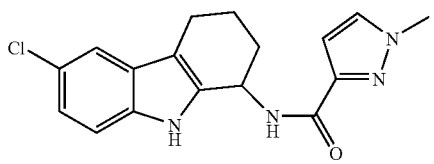

N-(6-Chloro-2,3,4,9-tetrahydro-1H-carbazol-1-yl)-1-methyl-1H-pyrazole-3-carboxamide was prepared from 1-methyl-1H-pyrazole-3-carboxylic acid and 6-chloro-2,3,4,9-tetrahydro-1H-carbazol-1-amine in a similar manner as described above to give an off-white solid (20% yield). $^1$H-NMR (CDCl$_3$): δ 8.95 (s, 1H), 7.43 (m, 1H), 7.37 (m, 1H), 7.22 (d, 1H), 7.07 (dd, 1H), 6.80 (m, 1H), 5.30 (m, 1H), 3.88 (s, 3H), 2.71 (m, 2H), 2.27 (m, 1H), 1.97 (m, 3H); MS m/z 327 (M−1).

Example 50

N-(6-Chloro-2,3,4,9-tetrahydro-1H-carbazol-1-yl)-1H-imidazole-4-carboxamide

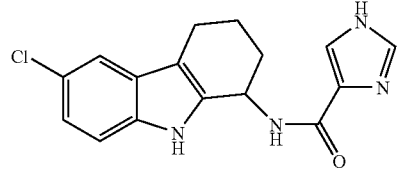

N-(6-Chloro-2,3,4,9-tetrahydro-1H-carbazol-1-yl)-1H-imidazole-4-carboxamide was prepared from 4-imidazole carboxylic acid and 6-chloro-2,3,4,9-tetrahydro-1H-carbazol-1-amine in a similar manner as described above to give a white solid (4% yield). $^1$H-NMR (CDCl$_3$): δ 9.19 (s, 1H), 7.62 (s, 1H), 7.57 (s, 1H), 7.41 (s, 1H), 7.37 (d, 1H), 7.17 (d, 1H), 7.05 (dd, 1H), 6.60 (d, 1H), 5.25 (m, 1H), 2.62 (m, 2H), 2.21 (m, 1H), 1.91 (m, 3H); MS m/z 313 (M−1).

Example 51

N-(6-Chloro-2,3,4,9-tetrahydro-1H-carbazol-1-yl)-1H-pyrazole-3-carboxamide

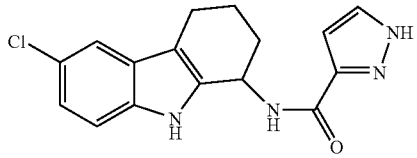

N-(6-Chloro-2,3,4,9-tetrahydro-1H-carbazol-1-yl)-1H-pyrazole-3-carboxamide was prepared from 1H-pyrazole-3-carboxylic acid and 6-chloro-2,3,4,9-tetrahydro-1H-carbazol-1-amine in a similar manner as described above to give a white solid (16% yield). $^1$H-NMR (CD$_3$OD-d$_4$): δ 7.70 (d, 1H), 7.37 (d, 1H), 7.22 (d, 1H), 6.99 (dd, 1H), 6.81 (d, 1H), 5.37 (m, 1H), 2.70 (m, 2H), 2.19 (m, 1H), 2.00 (m, 3H); MS m/z 313 (M−1).

Example 52

N-(6-bromo-2,3,4,9-tetrahydro-1H-carbazol-1-yl)-2,6-difluorobenzamide

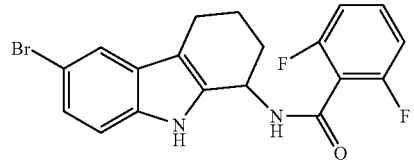

N-(6-bromo-2,3,4,9-tetrahydro-1H-carbazol-1-yl)-2,6-difluorobenzamide was prepared from 2,6-difluorobenzoyl-chloride and 6-bromo-2,3,4,9-tetrahydro-1H-carbazol-1-amine in a similar manner as described above to give a white solid: $^1$H-NMR (CDCl$_3$): δ 8.80 (s, 1H), 7.60 (m, 1H), 7.35 (m, 1H), 7.23 (overlapped dd and d, 2H), 6.94 (t, 2H), 6.37 (d, 1H), 5.35 (m, 1H), 2.7 (m, 2H), 2.26 (m, 1H), 1.95 (m, 3H); MS m/z 404 (M−1).

Example 53

N-(6-bromo-2,3,4,9-tetrahydro-1H-carbazol-1-yl)-2-fluorobenzenesulfonamide

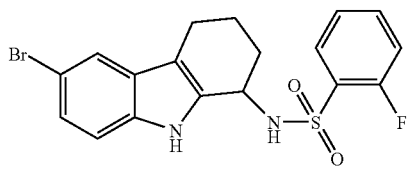

N-(6-bromo-2,3,4,9-tetrahydro-1H-carbazol-1-yl)-2-fluorobenzenesulfonamide was prepared from 2-fluorobenzenesulfonylchloride and 6-bromo-2,3,4,9-tetrahydro-1H-carbazol-1-amine in a similar manner as described above to give a white solid: $^1$H-NMR (CDCl$_3$): δ 8.56 (s, 1H), 8.00 (m, 1H), 7.65 (m, 1H), 7.58 (m, 1H), 7.2-7.4 (m, 3H), 5.04 (d, 1H), 4.60 (m, 1H), 2.65 (m, 2H), 1.6-2.1 (m, 4H); MS m/z 421 (M−1).

Example 54

N-(6-bromo-2,3,4,9-tetrahydro-1H-carbazol-1-yl)-2,6-difluorobenzenesulfonamide

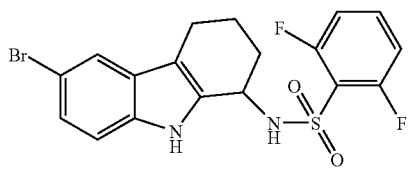

N-(6-bromo-2,3,4,9-tetrahydro-1H-carbazol-1-yl)-2,6-difluorobenzenesulfonamide was prepared from 2,6-difluorobenzenesulfonylchloride and 6-bromo-2,3,4,9-tetrahydro-1H-carbazol-1-amine in a similar manner as described above to give a white solid: $^1$H-NMR (CDCl$_3$): δ 8.60 (s, 1H), 7.48-7.58 (m, 2H), 7.24 (dd, 1H), 7.18 (d, 1H), 7.04 (t, 1H), 5.31 (m, 1H), 4.73 (m, 1H), 2.62 (m, 2H), 1.7-2.1 (m, 4H).

BIOLOGICAL EXPERIMENTALS AND DATA

Compounds of the current invention are believed useful in the treatment and/or prophylaxis of conditions and diseases associated with HPV infection. Activity mediated through HPV was determined using the following W-12 cellular assay.

Cell Culture and Medium

The W12 cell line used contains HPV16 DNA and was derived from a low-grade cervical dysplasia tissue by Margaret Stanley and subsequently clonally selected by Paul Lambert (University of Wisconsin). One of these clones, W12-20850, contains 1000 copies of episomal HPV16 DNA and was used in the cell-based assay. W12-20850 cells were routinely cultured with a gamma-irradiated (6000 rads) feeder layer of 3T3 cells. Assays, however, were run in the absence of a 3T3 feeder layer. W12-20850 and 3T3 cells were routinely split when they were sub-confluent. W12-20850 were grown in W12 Medium which is constituted of 25% DMEM (Gibco BRL, Cat # 12430-047), 75% F12 Media (Gibco BRL, Cat # 11765-021) and 2.5% FBS. The additives include 24.0 mg/ml Adenine (Sigma, Cat # A-9795), 0.4 mg/ml Hydrocortisone (Calbiochem, Cat # 386698), 5.0 mg/ml Bovine Insulin (Sigma, Cat # I-1882), 8.4 ng/ml cholera toxin (Fluka, Cat # 26694) and 10 ng/ml EGF (Invitrogen, Cat # 13247-051). 3T3 cells were grown in DMEM containing 10% FBS. Cell lines were incubated at 37° C., in the presence of 5% CO$_2$.

Cell Based Assay

For the assay, W12-20850 cells were seeded into a 96 well plate-containing compound. Plates were incubated at 37° C. in the presence of 5% CO$_2$, for four days. On the fourth day, cells were lysed and the amount of episomal HPV-16 DNA was quantified using a non-radioactive hybrid capture technique with HPV-16 specific capture and detection probes. The percent inhibition relative to untreated control cells was then determined.

Hybrid Capture

The hybrid capture assay is run in a 96 well plate format. Hybridization plates (Nunc Maxisorb Cat # 450320) were coated with a mixture of capture probe and ReactiBind solution for at least 4 hours and then washed with 0.2)(SSC, 0.05% Tween20 (SSCT) prior to blocking with 150 μl/well of 0.2 N NaOH, 1% Igepal, 10 mg/ml hsDNA for 6-8 hours. The hybridization was carried out by mixing 271 μl of lysed cells with 45 μl of denatured detection probe in 6M guanidine isothiocyanate. To prevent evaporation, 50 μl of mineral oil was added to each well. The plate was then heated to 90° C. for 6.5 minutes and the hybridization continued at 42° C. overnight. Assay plates were washed 6 times with SSC/T. Anti-digoxigenin HRP-conjugated Ab (Boehringer Mannheim 1207733, 1:5000) was incubated in the wells for 30 min at room temperature and washed with PBS/0.05% Tween-20. SuperSignal LBA substrate (Pierce Cat # 37070) was added, and chemiluminescence was measured using Wallac 1420 Victor plate reader.

| Example | W-12 (nM) |
|---|---|
| 9 | 548 |
| 10 | 24000 |
| 11 | >1000 |
| 12 | >10000 |
| 13 | 237 |
| 14A | 32 |
| 14B | 10 |
| 14C | 5000 |
| 15 | 580 |
| 16 | 1200 |
| 17 | 318 |
| 18 | 44 |
| 19 | 5800 |
| 20 | 20 |
| 21 | 22 |
| 22 | 45 |
| 23 | 17 |
| 24 | 8 |
| 25 | 58 |
| 26 | 14 |
| 27 | 28 |
| 28 | 23 |
| 29 | 9 |
| 30 | >10000 |
| 31 | >7300 |
| 32 | 1400 |
| 33 | 497 |
| 34 | >10000 |
| 35 | 184 |
| 36A | 60 |

-continued

| Example | W-12 (nM) |
|---|---|
| 36B | 20 |
| 36C | >10000 |
| 37 | 24 |
| 38 | <10 |
| 39 | 130 |
| 40 | 24 |
| 41 | 180 |
| 42 | >10000 |
| 43 | >10000 |
| 44 | 1700 |
| 45A | 10 |
| 45B | 5 |
| 45C | 6000 |
| 46A | 12 |
| 46B | 7 |
| 46C | >3000 |
| 47 | 810 |
| 48 | 2240 |
| 49 | 1650 |
| 50 | 440 |
| 51 | 73 |
| 52 | 45 |
| 53 | 51 |
| 54 | 94 |

Test compounds were employed in free or salt form.

All research complied with the principles of laboratory animal care (NIH publication No. 85-23, revised 1985) and GlaxoSmithKline policy on animal use.

Although specific embodiments of the present invention are herein illustrated and described in detail, the invention is not limited thereto. The above detailed descriptions are provided as exemplary of the present invention and should not be constructed as constituting any limitation of the invention. Modifications will be obvious to those skilled in the art, and all modifications that do not depart from the spirit of the invention are intended to be included with the scope of the appended claims.

What is claimed is:

1. A compound of formula (I):

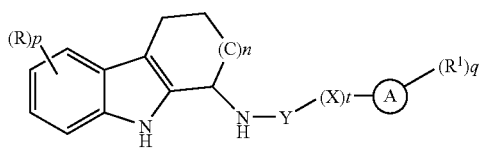

(I)

wherein:
n is 0, 1, or 2;
t is 0 or 1;
X is —NH—, —O—, —R$^{10}$—, —R$^{10}$O—, —R$^{10}$OR$^{10}$—, —NR$^{10}$—, —R$^{10}$N—, —R$^{10}$NR$^{10}$—, —R$^{10}$S(O)$_m$—, or —R$^{10}$S(O)$_m$R$^{10}$—;
Y is —S(O)$_m$—;
each R is the same or different and is independently selected from the group consisting of
halogen, haloalkyl, alkyl, alkenyl, alkynyl, cycloalkyl, cycloalkenyl, —R$^{10}$cycloalkyl, Ay, —NHR$^{10}$Ay, Het, —NHHet, —NHR$^{10}$Het, —OR$^2$, —OAy, —OHet, —R$^{10}$OR$^2$, —NR$^2$R$^3$, —NR$^2$Ay, —R$^{10}$NR$^2$R$^3$, —R$^{10}$NR$^2$Ay, —R$^{10}$C(O)R$^2$, —C(O)R$^2$, —CO$_2$R$^2$, —R$^{10}$CO$_2$R$^2$, —C(O)NR$^2$R$^3$, —C(O)Ay, —C(O)NR$^2$Ay, —C(O)Het, —C(O)NHR$^{10}$Het, —R$^{10}$C(O)NR$^2$R$^3$, —C(S)NR$^2$R$^3$, —R$^{10}$C(S)NR$^2$R$^3$, —R$^{10}$NHC(NH)NR$^2$R$^3$, —C(NH)NR$^2$R$^3$, —R$^{10}$C(NH)NR$^2$R$^3$, —S(O)$_2$NR$^2$R$^3$, —S(O)$_2$NR$^2$Ay, —R$^{10}$SO$_2$NHCOR$^2$, —R$^{10}$SO$_2$NR$^2$R$^3$, —R$^{10}$SO$_2$R$^2$, —S(O)$_m$R$^2$, —S(O)$_m$Ay, cyano, nitro, or azido;

each R$^1$ is the same or different and is independently selected from the group consisting of halogen, haloalkyl, alkyl, alkenyl, alkynyl, cycloalkyl, cycloalkenyl, —R$^{10}$cycloalkyl, Ay, —NHR$^{10}$Ay, Het, —NHHet, —NHR$^{10}$Het, —OR$^2$, —OAy, —OHet, —R$^{10}$OR$^2$, —NR$^2$R$^3$, —NR$^2$Ay, —R$^{10}$NR$^2$R$^3$, —R$^{10}$NR$^2$Ay, —R$^{10}$C(O)R$^2$, —C(O)R$^2$, —CO$_2$R$^2$, —R$^{10}$CO$_2$R$^2$, —C(O)NR$^2$R$^3$, —C(O)Ay, —C(O)NR$^2$Ay, —C(O)Het, —C(O)NHR$^{10}$Het, —R$^{10}$C(O)NR$^2$R$^3$, —C(S)NR$^2$R$^3$, —R$^{10}$C(S)NR$^2$R$^3$, —R$^{10}$NHC(NH)NR$^2$R$^3$, —C(NH)NR$^2$R$^3$, —R$^{10}$C(NH)NR$^2$R$^3$, —S(O)$_2$NR$^2$R$^3$, —S(O)$_2$NR$^2$Ay, —R$^{10}$SO$_2$NHCOR$^2$, —R$^{10}$SO$_2$NR$^2$R$^3$, —R$^{10}$SO$_2$R$^2$, —S(O)$_m$R$^2$, —S(O)$_m$Ay, cyano, nitro, or azido;

each m independently is 0, 1, or 2;
each R$^{10}$ is the same or different and is independently selected from alkylene, cycloalkylene, alkenylene, cycloalkenylene, and alkynylene;
p and q are each independently selected from 0, 1, 2, 3, 4, or 5;
each of R$^2$ and R$^3$ are the same or different and are independently selected from the group consisting of H, alkyl, alkenyl, alkynyl, cycloalkyl, cycloalkenyl, —R$^{10}$cycloalkyl, —R$^{10}$OH, —R$^{10}$(OR$^{10}$)$_w$, and —R$^{10}$NR$^4$R$^5$;
w is 1-10;
each of R$^4$ and R$^5$ are the same or different and are independently selected from the group consisting of alkyl, cycloalkyl, alkenyl, cycloalkenyl, and alkynyl;
Ay represents an aryl group;
Het represents a 5- or 6-membered heterocyclyl or heteroaryl group;
ring A is aryl or heteroaryl;
provided that when the A ring is aryl, t is 0, and Y is SO$_2$, then p is not 0; or a pharmaceutically acceptable salt or solvate thereof.

2. The compound of claim 1 wherein alkyl is C$_1$-C$_6$ alkyl, alkoxy is C$_1$-C$_6$ alkoxy, haloalkyl is C$_1$-C$_6$ haloalkyl, alkylene is C$_1$-C$_6$ alkylene, and alkenylene is C$_1$-C$_6$ alkenylene.

3. The compound of claim 1 wherein t is 1 and X is —NH—, —O—, or —R$^{10}$.

4. The compound of claim 1 wherein p is 1 or more and R is selected from halogen, alkyl, haloalkyl, —OR$^2$, —NR$^2$R$^3$, —C(O)R$^2$, —CO$_2$R$^2$, cyano, nitro, or azido.

5. The compound of claim 4 wherein R is halogen, alkyl, haloalkyl.

6. The compound of claim 5 wherein R is substituted para to the depicted N atom.

7. The compound of claim 6 wherein R is halogen.

8. The compound of claim 7 wherein R is Br or Cl.

9. The compound of claim 1 wherein q is 1 or more and R$^1$ is selected from halogen, alkyl, haloalkyl, —OR$^2$, —NR$^2$R$^3$, —C(O)R$^2$, —CO$_2$R$^2$, Ay, Het, cyano, nitro, or azido.

10. The compound of claim 9 wherein R$^1$ is selected from halogen, alkyl, haloalkyl, —OR$^2$, —NR$^2$R$^3$, —C(O)R$^2$, —CO$_2$R$^2$, or cyano.

11. The compound of claim 10 wherein R$^2$ and R$^3$ each are C$_1$-C$_6$ alkyl.

12. The compound of claim 10 wherein R$^1$ is selected from halogen, alkyl, or —OR$^2$.

13. The compound of claim 12 wherein said halogen is fluoro or chloro, said alkyl is methyl, and said —OR² is alkoxy.

14. The compound of claim 13 wherein q is 1 or more and R¹ is selected from halogen, alkyl, haloalkyl, —OR², —NR²R³, —C(O)R², —CO₂R², Ay, Het, cyano, nitro, or azido.

15. The compound of claim 14 wherein q is 1 or more and R¹ is selected from halogen, alkyl, haloalkyl, —OR², —NR²R³, —C(O)R², —CO₂R², or cyano.

16. The compound of claim 1 wherein the A ring is heteroaryl.

17. The compound of claim 16 wherein the heteroaryl is pyridyl.

18. The compound of claim 17 wherein q is 0 or 1.

19. The compound of claim 18 wherein when q is 1, then R¹ is selected from halogen, alkyl, haloalkyl, —OR², —NR²R³, —C(O)R², —CO₂R², Ay, Het, cyano, nitro, or azido.

20. The compound of claim 19 wherein when q is 1, then R¹ is selected from halogen, alkyl, haloalkyl, —OR², —NR²R³, —C(O)R², —CO₂R², or cyano.

21. A compound selected from:

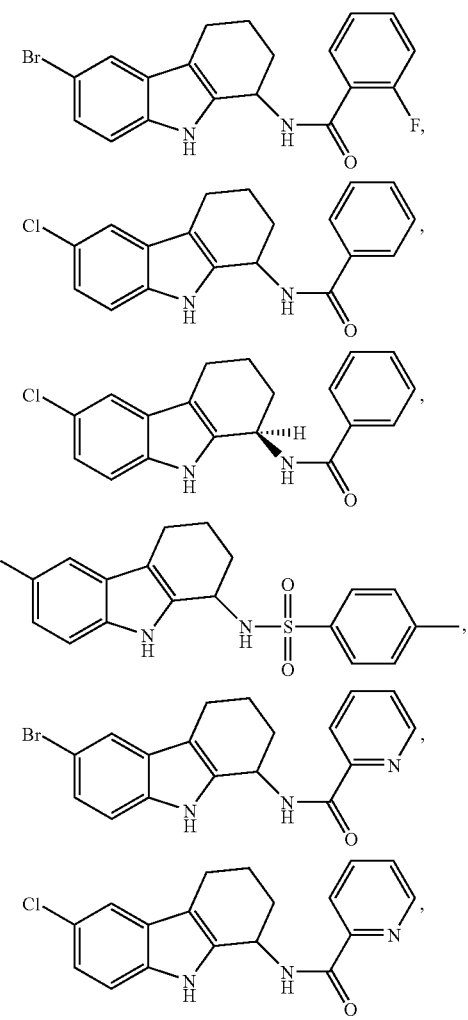

-continued

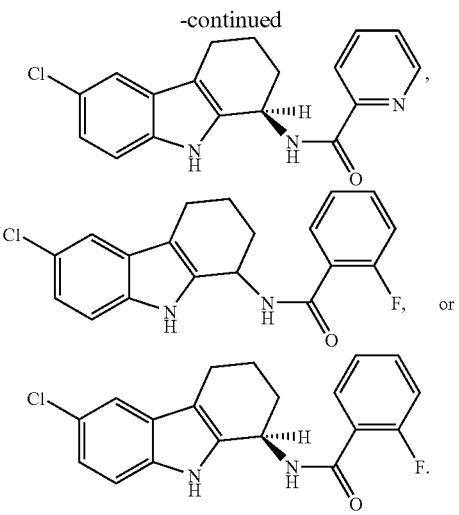

22. A compound selected from the group consisting of:
N-(6-Bromo-2,3,4,9-tetrahydro-1H-carbazol-1-yl)-N'-phenylurea;
N-(6-Bromo-2,3,4,9-tetrahydro-1H-carbazol-1-yl)-N'-(4-methoxyphenyl)urea;
N-(6-Bromo-2,3,4,9-tetrahydro-1H-carbazol-1-yl)-N'-(4-methoxy-2-methylphenyl)urea;
N-(6-Bromo-2,3,4,9-tetrahydro-1H-carbazol-1-yl)-N'-(3-chloro-4-methoxyphenyl)urea;
N-(6-Bromo-2,3,4,9-tetrahydro-1H-carbazol-1-yl)-N'-[4-(dimethylamino)phenyl]urea;
N-(6-Bromo-2,3,4,9-tetrahydro-1H-carbazol-1-yl)benzamide;
N-[(1R)-6-bromo-2,3,4,9-tetrahydro-1H-carbazol-1-yl]benzamide;
N-[(1S)-6-bromo-2,3,4,9-tetrahydro-1H-carbazol-1-yl]benzamide;
N-(6-Bromo-2,3,4,9-tetrahydro-1H-carbazol-1-yl)-2-phenylacetamide;
N-(6-Bromo-2,3,4,9-tetrahydro-1H-carbazol-1-yl)-3-phenylpropanamide;
N-(6-Bromo-2,3,4,9-tetrahydro-1H-carbazol-1-yl)-3-phenylprop-2-enamide;
Benzyl 6-bromo-2,3,4,9-tetrahydro-1H-carbazol-1-ylcarbamate;
N-(6-Bromo-2,3,4,9-tetrahydro-1H-carbazol-1-yl)-2,6-dichlorobenzamide;
N-(6-Bromo-2,3,4,9-tetrahydro-1H-carbazol-1-yl)4-fluorobenzamide;
N-(6-Bromo-2,3,4,9-tetrahydro-1H-carbazol-1-yl)-4-methoxybenzamide;
N-(6-Bromo-2,3,4,9-tetrahydro-1H-carbazol-1-yl)4-nitrobenzamide;
N-(6-Bromo-2,3,4,9-tetrahydro-1H-carbazol-1-yl)4-chlorobenzamide;
N-(6-Bromo-2,3,4,9-tetrahydro-1H-carbazol-1-yl)4-methylbenzamide;
N-(6-Bromo-2,3,4,9-tetrahydro-1H-carbazol-1-yl)-4-(trifluoromethyl)benzamide;
N-(6-Bromo-2,3,4,9-tetrahydro-1H-carbazol-1-yl)-3-fluorobenzamide;
N-(6-Bromo-2,3,4,9-tetrahydro-1H-carbazol-1-yl)-3-methoxybenzamide;
N-(6-Bromo-2,3,4,9-tetrahydro-1H-carbazol-1-yl)-3-methylbenzamide;

N-(6-Bromo-2,3,4,9-tetrahydro-1H-carbazol-1-yl)-2-fluorobenzamide;
N-(6-Bromo-2,3,4,9-tetrahydro-1H-carbazol-1-yl)-2-methoxybenzamide;
N-(6-Bromo-2,3,4,9-tetrahydro-1H-carbazol-1-yl)-2-nitrobenzamide;
N-(6-Bromo-2,3,4,9-tetrahydro-1H-carbazol-1-yl)-2-chlorobenzamide;
N-(6-Bromo-2,3,4,9-tetrahydro-1H-carbazol-1-yl)-2-methylbenzamide;
N-(2,3,4,9-Tetrahydro-1H-carbazol-1-yl)benzamide;
N-(6-Methyl-2,3,4,9-tetrahydro-1H-carbazol-1-yl)benzamide;
N-(6-Chloro-2,3,4,9-tetrahydro-1H-carbazol-1-yl)benzamide;
N-[(1R)-6-chloro-2,3,4,9-tetrahydro-1H-carbazol-1-yl]benzamide;
N-[(1S)-6-chloro-2,3,4,9-tetrahydro-1H-carbazol-1-yl]benzamide;
N-(6-Bromo-2,3,4,9-tetrahydro-1H-carbazol-1-yl)-4-methylbenzenesulfonamide;
N-(6-Bromo-2,3,4,9-tetrahydro-1H-carbazol-1-yl)pyridine-2-carboxamide;
N-(6-Bromo-2,3,4,9-tetrahydro-1H-carbazol-1-yl)nicotinamide;
N-(6-Bromo-2,3,4,9-tetrahydro-1H-carbazol-1-yl)-6-chloronicotinamide;
N-(6-Bromo-2,3,4,9-tetrahydro-1H-carbazol-1-yl)isonicotinamide;
N-Phenyl-N'-(2,3,4,9-tetrahydro-1H-carbazol-1-yl)urea;
N-(6-Methyl-2,3,4,9-tetrahydro-1H-carbazol-1-yl)-N'-phenylurea;
N-(6-Chloro-2,3,4,9-tetrahydro-1H-carbazol-1-yl)-N'-phenylurea;
N-(6-Chloro-2,3,4,9-tetrahydro-1H-carbazol-1-yl)-2-pyridinecarboxamide;
N-[(1R)-6-chloro-2,3,4,9-tetrahydro-1H-carbazol-1-yl]pyridine-2-carboxamide;
N-[(1S)-6-chloro-2,3,4,9-tetrahydro-1H-carbazol-1-yl]pyridine-2-carboxamide;
N-(6-Chloro-2,3,4,9-tetrahydro-1H-carbazol-1-yl)-2-fluorobenzamide;
N-[(1R)-6-chloro-2,3,4,9-tetrahydro-1H-carbazol-1-yl]-2-fluorobenzamide;
N-[(1S)-6-chloro-2,3,4,9-tetrahydro-1H-carbazol-1-yl]-2-fluorobenzamide;
N-(6-Chloro-2,3,4,9-tetrahydro-1H-carbazol-1-yl)-1-methyl-1H-imidazole-5-carboxamide;
N-(6-Chloro-2,3,4,9-tetrahydro-1H-carbazol-1-yl)-1-methyl-1H-pyrazole-5-carboxamide;
N-(6-Chloro-2,3,4,9-tetrahydro-1H-carbazol-1-yl)-1-methyl-1H-pyrazole-3-carboxamide;
N-(6-Chloro-2,3,4,9-tetrahydro-1H-carbazol-1-yl)-1H-imidazole-4-carboxamide;
N-(6-Chloro-2,3,4,9-tetrahydro-1H-carbazol-1-yl)-1H-pyrazole-3-carboxamide;
N-(6-bromo-2,3,4,9-tetrahydro-1H-carbazol-1-yl)-2,6-difluorobenzamide;
N-(6-bromo-2,3,4,9-tetrahydro-1H-carbazol-1-yl)-2-fluorobenzenesulfonamide; and
N-(6-bromo-2,3,4,9-tetrahydro-1H-carbazol-1-yl)-2,6-difluorobenzenesulfonamide.

23. A compound selected from the group consisting of:
N-(6-Bromo-2,3,4,9-tetrahydro-1H-carbazol-1-yl)-N'-[4-(dimethylamino)phenyl]urea;
N-(6-Bromo-2,3,4,9-tetrahydro-1H-carbazol-1-yl)benzamide;
N-[(1R)-6-bromo-2,3,4,9-tetrahydro-1H-carbazol-1-yl]benzamide;
N-(6-Bromo-2,3,4,9-tetrahydro-1H-carbazol-1-yl)-3-phenylprop-2-enamide;
Benzyl 6-bromo-2,3,4,9-tetrahydro-1H-carbazol-1-ylcarbamate;
N-(6-Bromo-2,3,4,9-tetrahydro-1H-carbazol-1-yl)4-fluorobenzamide;
N-(6-Bromo-2,3,4,9-tetrahydro-1H-carbazol-1-yl)4-methoxybenzamide;
N-(6-Bromo-2,3,4,9-tetrahydro-1H-carbazol-1-yl)4-nitrobenzamide;
N-(6-Bromo-2,3,4,9-tetrahydro-1H-carbazol-1-yl)4-chlorobenzamide;
N-(6-Bromo-2,3,4,9-tetrahydro-1H-carbazol-1-yl)-4-methylbenzamide;
N-(6-Bromo-2,3,4,9-tetrahydro-1H-carbazol-1-yl)-4-(trifluoromethyl)benzamide;
N-(6-Bromo-2,3,4,9-tetrahydro-1H-carbazol-1-yl)-3-fluorobenzamide;
N-(6-Bromo-2,3,4,9-tetrahydro-1H-carbazol-1-yl)-3-methoxybenzamide;
N-(6-Bromo-2,3,4,9-tetrahydro-1H-carbazol-1-yl)-3-methylbenzamide;
N-(6-Bromo-2,3,4,9-tetrahydro-1H-carbazol-1-yl)-2-fluorobenzamide;
N-(6-Bromo-2,3,4,9-tetrahydro-1H-carbazol-1-yl)-2-methylbenzamide;
N-(6-Methyl-2,3,4,9-tetrahydro-1H-carbazol-1-yl)benzamide;
N-(6-Chloro-2,3,4,9-tetrahydro-1H-carbazol-1-yl)benzamide;
N-[(1R)-6-chloro-2,3,4,9-tetrahydro-1H-carbazol-1-yl]benzamide;
N-(6-Bromo-2,3,4,9-tetrahydro-1H-carbazol-1-yl)-4-methylbenzenesulfonamide;
N-(6-Bromo-2,3,4,9-tetrahydro-1H-carbazol-1-yl)pyridine-2-carboxamide;
N-(6-Bromo-2,3,4,9-tetrahydro-1H-carbazol-1-yl)nicotinamide;
N-(6-Bromo-2,3,4,9-tetrahydro-1H-carbazol-1-yl)-6-chloronicotinamide;
N-(6-Bromo-2,3,4,9-tetrahydro-1H-carbazol-1-yl)isonicotinamide;
N-(6-Chloro-2,3,4,9-tetrahydro-1H-carbazol-1-yl)-2-pyridinecarboxamide;
N-[(1R)-6-chloro-2,3,4,9-tetrahydro-1H-carbazol-1-yl]pyridine-2-carboxamide;
N-(6-Chloro-2,3,4,9-tetrahydro-1H-carbazol-1-yl)-2-fluorobenzamide;
N-[(1R)-6-chloro-2,3,4,9-tetrahydro-1H-carbazol-1-yl]-2-fluorobenzamide;
N-(6-Chloro-2,3,4,9-tetrahydro-1H-carbazol-1-yl)-1H-imidazole-4-carboxamide;
N-(6-Chloro-2,3,4,9-tetrahydro-1H-carbazol-1-yl)-1H-pyrazole-3-carboxamide;
N-(6-bromo-2,3,4,9-tetrahydro-1H-carbazol-1-yl)-2,6-difluorobenzamide;
N-(6-bromo-2,3,4,9-tetrahydro-1H-carbazol-1-yl)-2-fluorobenzenesulfonamide; and
N-(6-bromo-2,3,4,9-tetrahydro-1H-carbazol-1-yl)-2,6-difluorobenzenesulfonamide.

24. A compound selected from the group consisting of:
N-(6-Bromo-2,3,4,9-tetrahydro-1H-carbazol-1-yl)benzamide;
N-[(1R)-6-bromo-2,3,4,9-tetrahydro-1H-carbazol-1-yl]benzamide;

Benzyl 6-bromo-2,3,4,9-tetrahydro-1H-carbazol-1-ylcarbamate;
N-(6-Bromo-2,3,4,9-tetrahydro-1H-carbazol-1-yl)-4-fluorobenzamide;
N-(6-Bromo-2,3,4,9-tetrahydro-1H-carbazol-1-yl)-4-methoxybenzamide;
N-(6-Bromo-2,3,4,9-tetrahydro-1H-carbazol-1-yl)-4-nitrobenzamide;
N-(6-Bromo-2,3,4,9-tetrahydro-1H-carbazol-1-yl)-4-chlorobenzamide;
N-(6-Bromo-2,3,4,9-tetrahydro-1H-carbazol-1-yl)-4-methylbenzamide;
N-(6-Bromo-2,3,4,9-tetrahydro-1H-carbazol-1-yl)-3-fluorobenzamide;
N-(6-Bromo-2,3,4,9-tetrahydro-1H-carbazol-1-yl)-3-methoxybenzamide;
N-(6-Bromo-2,3,4,9-tetrahydro-1H-carbazol-1-yl)-3-methylbenzamide;
N-(6-Bromo-2,3,4,9-tetrahydro-1H-carbazol-1-yl)-2-fluorobenzamide;
N-(6-chloro-2,3,4,9-tetrahydro-1H-carbazol-1-yl)benzamide;
N-[(1R)-6-chloro-2,3,4,9-tetrahydro-1H-carbazol-1-yl]benzamide;
N-(6-Bromo-2,3,4,9-tetrahydro-1H-carbazol-1-yl)-4-methylbenzenesulfonamide;
N-(6-Bromo-2,3,4,9-tetrahydro-1H-carbazol-1-yl)pyridine-2-carboxamide;
N-(6-Bromo-2,3,4,9-tetrahydro-1H-carbazol-1-yl)-6-chloronicotinamide;
N-(6-Chloro-2,3,4,9-tetrahydro-1H-carbazol-1-yl)-2-pyridinecarboxamide;
N-[(1R)-6-chloro-2,3,4,9-tetrahydro-1H-carbazol-1-yl]pyridine-2-carboxamide;
N-(6-Chloro-2,3,4,9-tetrahydro-1H-carbazol-1-yl)-2-fluorobenzamide;
N-[(1R)-6-chloro-2,3,4,9-tetrahydro-1H-carbazol-1-yl]-2-fluorobenzamide;
N-(6-bromo-2,3,4,9-tetrahydro-1H-carbazol-1-yl)-2,6-difluorobenzamide; and
N-(6-bromo-2,3,4,9-tetrahydro-1H-carbazol-1-yl)-2-fluorobenzenesulfonamide.

25. A pharmaceutical composition comprising a compound according to any of claims 22 to 24, and a pharmaceutically acceptable carrier.

26. A method for the treatment of a papovavirus infection selected from the group consisting of polyoma virus infection and papilloma virus infection comprising administering to a subject in need thereof a therapeutically effective amount of a compound according to any of claims 22 to 24.

27. A method for the treatment of conditions or disorders due to HPV infection selected from the group consisting of genital warts and cervical dysplasia, comprising administering to a subject in need thereof a therapeutically effective amount of a compound according to any of claims 22 to 24.

* * * * *